US005523217A

United States Patent [19]
Lupski et al.

[11] Patent Number: 5,523,217
[45] Date of Patent: Jun. 4, 1996

[54] FINGERPRINTING BACTERIAL STRAINS USING REPETITIVE DNA SEQUENCE AMPLIFICATION

[75] Inventors: James R. Lupski; Thearith Koeuth; James Versalovic, all of Houston, Tex.

[73] Assignee: Baylor College of Medicine, Houston, Tex.

[21] Appl. No.: 248,848

[22] Filed: May 25, 1994

Related U.S. Application Data

[63] Continuation of Ser. No. 781,424, Oct. 23, 1991, abandoned.
[51] Int. Cl.$^6$ .................... C12P 19/34; C12Q 1/68; C07H 21/04
[52] U.S. Cl. .................... 435/91.2; 435/6; 536/24.33; 536/24.32; 935/77; 935/78
[58] Field of Search .................... 435/6, 91.2; 536/24.33, 536/24.32; 935/77, 78

[56] References Cited

PUBLICATIONS

Versalovic et al. (1991) Nucleic Acids Research, vol. 19, No. 24, pp. 6823–6831.
Ledbetter et al. (1990) Genomics, vol. 6, pp. 475–481.
Welsh et al. (1991) Nucleic Acids Res. 19(4):861–865.
Austin, D. and Larson, T. J. (1991). Nucleotide sequence of the glpD gene encoding aerobic sn-glycerol 3-phosphate dehydrogenase of *Escherichia coli* K-12. *J. Bacteriol* 173:101–107.
Bachmann, B. J. (1990). Linkage map of *Escherichia coli* K–12, edition 8. *Microbiol Rev* 54:130–197.
Brosius, J. (1991). Retroposons—Seeds of Evolution. *Science* 251:753.
Carriere, C., Allardet-Servent, A., Bourg, G., Audurier, A., and Ramuz, M. (1991). DNA polymorphism in strains of *Listeria monocytogenes. J. Clin Microbiol* 29:1351–1355.
Chu, F. K., Maley, G. F., Maley, F., and Belfort, M. (1984). Intervening sequence in the thymidylate synthase gene of bacteriophage T4. *Proc Natl Acad Sci USA* 81:3049–3053.
Correia, F. F., Inouye, S. and Inouye, M. (1986). A 26-base--pair repetitive sequence specific for *Neisseria gonorrhoeae* and *Neisseria meningitidis* genomic DNA. *J Bacteriol* 167:1009–1015.
Dahl, M. K., Francoz, E., Saurin, W., Boos, W., Manson, M. D., and Hofnung, M. (1989). Comparison of sequences from the malB regions of *Salmonella typhimurium* and *Enterobacter aerogenes* with *Escherichia coli* K12: A potential new regulatory site in the interoperonic region. *Mol Gen Genet* 218:199–207.
Doolittle, W. F. (1978). Genes in pieces: were they ever together? *Nature* 272:581–582.
Eisenach, K. D., Cave, M. D., Bates, J. H. and Crawford, J. T. (1990). Polymerase chain reaction amplification of a repetitive DNA sequence specific for *Mycobacterium tuberculosis. J Infect Dis* 161:977–981.

Gilson, E., Bachellier, S., Perrin, S., Perrin, D., Grimont, P. A. D., Grimont, F. and Hofnung, M. (1990). Palindromic unit highly repetitive DNA sequences exhibit species specificity within *Enterobacteriaceae. Res Microbiol* 141:1103–1116.
Gilson, E., Clement, J.-M., Brutlag, D. and Hofnung, M. (1984). A family of dispersed repetitive extragenic palindromic DNA sequences in *E. coli. EMBO J* 3:1417–1421.
Gilson, E., Perrin, D. and Hofnung, M. (1990). DNA polymerase I and a protein complex bind specifically to *E. coli* palindromic unit highly repetitive DNA: implications for bacterial chromosome organization. *Nucl Acids Res* 18:3941–3952.
Gilson, E., Rousset, J. P., Clement, J. M. and Hofnung, M. (1986). A subfamily of *E. coli* palindromic units implicated in transcription termination? *Ann Inst Pasteur* 137B:259–270.
Glare, E. M., Paton, J. C., Premier, R. R., Lawrence, A. J. and Nisbet, I. T. (1990). Analysis of a repetitive DNA sequence from *Bordetella pertussis* and its application to the diagnosis of pertussis using the polymerase chain reaction. *J Clin Microbiol* 28:1982–1987.
Gott, J. M., Shub, D. A. and Belfort, M. (1986). Multiple self–splicing introns in bacteriophage T4: Evidence from autocatalytic GTP labeling of RNA in vitro. *Cell* 47:81–87.
Higgins, C. F., Ferro–Luzzi Ames, G., Barnes, W. M., Clement, J. M. and Hofnung, M. (1982). A novel intercistronic regulatory element of prokaryotic operons. *Nature* 298:760–762.
Higgins, C. F., McLaren, R. S. and Newbury, S. F. (1988). Repetitive extragenic palindromic sequences, mRNA stability and gene expression: evolution by gene conversion?—a review. *Gene* 72:3–14.
Houck, C. M., Rinehart, F. P. and Schmid, C. W. (1979). A ubiquitous family of repeated DNA sequences in the human genome. *J Mol Biol* 132:289–306.

(List continued on next page.)

Primary Examiner—W. Gary Jones
Assistant Examiner—Lisa Arthur
Attorney, Agent, or Firm—Fulbright & Jaworski

[57] ABSTRACT

Oligonucleotide primers and methods for identifying strains of bacteria by genomic fingerprinting are described. The methods are applicable to a variety of samples. The testing procedure includes amplifying the bacterial DNA in the sample to be tested by adding a pair of outwardly-directed primers to the sample. The primers are capable of hybridizing to repetitive DNA sequences in the bacterial DNA and extending outwardly from one hybridizable repetitive sequence to another hybridizable repetitive sequence. After amplification the extension products are separated by size and the specific strain of bacteria is determined by measuring the pattern of sized extension products. The procedure to identify strains of bacteria by fingerprinting has a variety of uses including: identifying bacteria in infections, agriculture and horticulture plots, bioremediation, food monitoring, production monitoring and quality assurance and quality control.

156 Claims, 17 Drawing Sheets

OTHER PUBLICATIONS

Hulton, C. S. J., Higgins, C. F. and Sharp, P. M. (1991). ERIC sequences: a novel family of repetitive elements in the genomes of *Escherichia coli, Salmonella typhimurium* and other Enterobacteria. *Mol Microbiol* 5:825–834.

Inouye, M. and Inouye, S. (1991). Retroelements in bacteria. *Trends Biochem Sci* 16:18–21.

Jelinek, W. R., Toomey, T. P., Leinwand, L., Duncan, C. H., Biro, P. A., Choudary, P. V., Weissman, S. M., Rubin, C. M., Houck, C. M., Deininger, P. L. and Schmid, C. W. (1980). Ubiquitous, interspersed repeated sequences in mammalian genomes. *Proc Natl Acad Sci USA* 77:1398–1402.

Kawase, Y., Iwai, S., Inoue, H., Miura, K. and Ohtsuka, E. (1986). Studies on nucleic acid interactions I. Stabilities of mini–duplexes $(dG_2A_4XA_4G_2.dC_2T_4YT_4C_2)$ and self-complementary d(GGGAAXYTTCCC) containing deoxyinosine and other mismatched bases. *Nucl Acids Res* 14:7727–7736.

Knoth, K., Roberds, S., Poteet, C. and Tamkun, M. (1988). Highly degenerate, inosine–containing primers specifically amplify rare cDNA using the polymerase chain reaction. *Nucl Acids Res* 16:10932.

Kohara, Y., Akiyama, K. and Isono, K. (1987). The physical map of the whole *E. coli* chromosome: application of a new strategy for rapid analysis and sorting of a large genomic library. *Cell* 50:495–508.

Kogan, S. C., Doherty, M. and Gitschier, J. (1987). An improved method for prenatal diagnosis of genetic diseases by analysis of amplified DNA sequences. *New England J Med.* 317:985–990.

Kuhsel, M. G., Strickland, R. and Palmer, J. D. (1990). An ancient group I intron shared by eubacteria and chloroplasts. *Science* 250:1570–1572.

Lawther, R. P., Wek, R. C., Lopes, J. M., Pereira, R., Taillon, B. E. and Hatfield, G. W. (1987). The complete nucleotide sequence of the ilvGMEDA operon of *Escherichia coli* K–12. *Nucl Acids Res* 15:2137–2155.

Lennon, E., Gutman, P. D., Yao, H. and Minton, K. W. (1991). A highly conserved repeated chromosomal sequence in the radioresistant bacterium *Deinococcus radiodurans* SARK. *J Bacteriol* 173:2137–2140.

Litwin, C. M., Storm, A. L., Chipowsky, S. and Ryan, K. J. (1991). Molecular epidemiology of *Shigella* infections: plasmid profiles, serotype correlation, and restriction endonuclease analysis. *J Clin Microbiol* 29:104–108.

Loenen, W. A. M., Daniel, Anne S., Braymer, H. D. and Murray, N. E. (1987). Organization and sequence of the hsd genes of *Escherichia coli* K–12. *J Mol Biol* 198:159–170.

Leuven, F. V. (1991). The trouble with PCR machines: fill up the empty spaces! *Trends in Genetics* 7:142.

Martin, F. H., Castro, M. M., Aboul–Ela, F., and Tinoco, Jr., I. (1985). Base pairing involving deoxyinosine: implications for probe design. *Nucl Acids Res* 13:8927–8938.

Mazel, D., Houmard, J., Castets, A. M. and de Marsac, N. Tandeau (1990). Highly repetitive DNA sequences in cyanobacterial genomes. *J Bacteriol* 172:2755–2761.

Miller, J. H. (1972). Experiments in molecular genetics. Cold Spring Harbor Laboratory.

Mullis, K. B. and Faloona, F. A. (1987). Specific synthesis of DNA in vitro via a polymerase–catalyzed chain reaction. *Methods in Enzymology* 155:335–350.

Murray, B. E., Singh, K. V., Heath, J. D., Sharma, B. R. and Weinstock, G. M. (1990). Comparison of genomic DNAs of different enterococcal isolates using restriction endonucleases with infrequent recognition sites. *J Clin Microbiol* 28:2059–2063.

Nelson, D. L., Ledbetter, S. A., Corbo, L., Victoria, M. F., Ramirez–Solis, R., Webster, T. D., Ledbetter, D. H. and Caskey, C. T. (1989). Alu polymerase chain reaction: A method for rapid isolation of human–specific sequences from complex DNA sources. *Proc Natl Acad Sci USA* 86:6686–6690.

Nesin, M., Lupski, J. R., Svec, P. and Godson, G. N. (1987). Possible new genes as revealed by molecular analysis of a 5–kb *Escherichia coli* chromosomal region 5 to the rpsU–dnaG–rpoD macromolecular synthesis operon. *Gene* 51:149–161.

Newbury, S. F., Smith, N. H., Robinson, E. C., Hiles, I. D. and Higgins, C. F. (1987). Stabilization of translationally active mRNA by prokaryotic REP sequences. *Cell* 48:297–310.

Noda, A., Courtright, J. B., Denor, P. F., Webb, G., Kohara, Y., and Ishihama, A. (1991). Rapid identification of specific genes in *E. coli* by hybridization to membranes containing the ordered set of phage clones. *Biotechniques* 10:474–477.

Owen, R. J. (1989). Chromosomal DNA fingerprinting—a new method of species and strain identification applicable to microbial pathogens. *J Med Microbiol* 30:89–99.

Rikke, B. A., Garvin, L. D. and Hardies, S. C. (1991). Systematic identification of LINE–1 repetitive DNA sequence differences having species specificity between *Mus spretus* and *Mus domesticus*. *J Mol Biol* 219:635–643.

Saiki, R. K., Scharf, S., Faloona, F., Mullis, K. B., Horn, G. T., Erlich, H. A. and Arnheim, N. (1985). Enzymatic amplification of β–globin genomic sequences and restriction site analysis for diagnosis of sickle cell anemia. *Science* 230:1350–1354.

Sapienza, C. and Doolittle, W. F. (1982). Unusual physical organization of the *Halobacterium* genome. *Nature* 295:384–389.

Scherer, S. and Stevens, D. A. (1988). A *Candida albicans* dispersed, repeated gene family and its epidemiologic applications. *Proc Natl Acad Sci USA* 85:1452–1456.

Schmid, C. W. and Jelinek, W. R. (1982). The Alu family of dispersed repetitive sequences. *Science* 216:1065–1070.

Sharples, G. J. and Lloyd, R. G. (1990). A novel repeated DNA sequence located in the intergenic regions of bacterial chromosomes. *Nucl Acids Res* 18:6503–6508.

Stern, M. J., Ferro–Luzzi Ames, G., Smith, N. H., Robinson, E. C. and Higgins, C. F. (1984). Repetitive extragenic palindromic sequences: a major component of the bacterial genome. *Cell* 37:1015–1026.

Stringer, S. L., Hong, S.–T., Giuntoli, D. and Stringer, J. R. (1991). Repeated DNA in *Pneumocystis carinii*. *J Clin Microbiol* 29:1194–1201.

Tabata, S., Higashitani, A., Takanami, M., Akiyama, K., Kohara, Y., Nishimura, Y., Nishimura, A., Yasuda, S. and Hirota, Y. (1989). Construction of an ordered cosmid collection of the *Escherichia coli* K–12 W3110 chromosome. *J Bacteriol* 171:1214–1218.

Versalovic, J., Koeuth, T., McCabe, E. R. B. and Lupski, J. R. (1991). Use of the polymerase chain reaction for physical mapping of *Escherichia coli* genes. *J Bacteriol* 173:5253–5255.

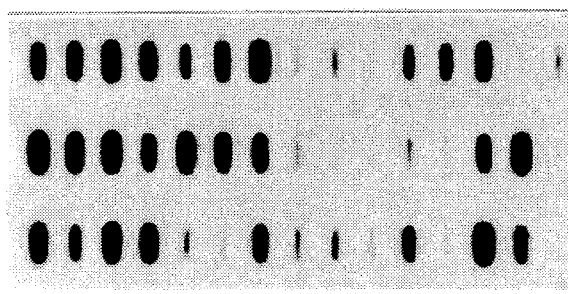

1. Rhodobacter sphaeroides
2. Rhizobium meliloti
3. Neisseria gonorrheae
4. Neisseria meningitidis
5. Sphaerotilus sp.
6. E. coli HB101
7. E. coli W3110
8. Salmonella sp.
9. Citrobacter diversus
10. Klebsiella pneumoniae
11. Enterobacter sakazakii
12. Serratia marcescens
13. Proteus vulgaris
14. Pseudomonas aeruginosa
15. Xanthomonas manihotis
16. Vibro vulnificus
17. Myxococcus xanthus
18. Arthrobacter luteus
19. Nocardia otitidiscaviarum
20. Streptomyces albus G
21. Mycobacterium aurum
22. Bacillus subtilis
23. Listeria monocytogenes
24. Staphylococcus aureus
25. Streptococcus pneumoniae
26. Group B Streptococcus
27. Caryophanon latum
28. Mycoplasma pneumoniae
29. Anabaena sp.
30. Borrelia burgdorferi
31. Treponema pallidum
32. Treponema phagedenis
33. Bacteroides fragilis
34. Fusobacterium nucleatum
35. Flavobacterium meningosepticum
36. Flavobacterium okeanokoites
37. Deinococcus radiophilus
38. Thermus aquaticus
39. Thermus thermophilus
40. Herpetosiphon giganteus
41. Halobacterium halobium
42. Saccharomyces cerevisiae
43. Schizosaccharomyces pombe
44. Candida parapsilosis
45. Homo sapiens

FIGURE 8

1. Rhodobacter sphaeroides
2. Rhizobium meliloti
3. Neisseria gonorrheae
4. Neisseria meningitidis
5. Sphaerotilus sp.
6. E. coli HB101
7. E. coli W3110
8. Salmonella sp.
9. Citrobacter diversus
10. Klebsiella pneumoniae
11. Enterobacter sakazakii
12. Serratia marcescens
13. Proteus vulgaris
14. Pseudomonas aeruginosa
15. Xanthomonas manihotis
16. Vibro vulnificus
17. Myxococcus xanthus
18. Arthrobacter luteus
19. Nocardia otitidiscaviarum
20. Streptomyces albus G
21. Mycobacterium aurum
22. Bacillus subtilis
23. Listeria monocytogenes
24. Staphylococcus aureus
25. Streptococcus pneumoniae
26. Group B Streptococcus
27. Caryophanon latum
28. Mycoplasma pneumoniae
29. Anabaena sp.
30. Borrelia burgdorferi
31. Treponema pallidum
32. Treponema phagedenis
33. Bacteroides fragilis
34. Fusobacterium nucleatum
35. Flavobacterium meningosepticum
36. Flavobacterium okeanokoites
37. Deinococcus radiophilus
38. Thermus aquaticus
39. Thermus thermophilus
40. Herpetosiphon giganteus
41. Halobacterium halobium
42. Saccharomyces cerevisiae
43. Schizosaccharomyces pombe
44. Candida parapsilosis
45. Homo sapiens

FIGURE 10

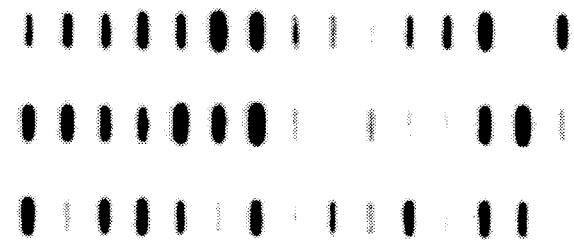

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =A, G, C or T"

( x i ) SEQUENCE DESCRIPTION: SEQ ID NO:1:

GCCKGATGNC GRCGYNNNNN RCGYCTTATC MGGCCTAC        38

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine"

( x i ) SEQUENCE DESCRIPTION: SEQ ID NO:2:

GCCNGATGNC GNCGNNNNNN NCGNCTTATC NGGCCTAC        38

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine"

( x i ) SEQUENCE DESCRIPTION: SEQ ID NO:3:

GCCKGATGNC GRCGYNNNNN RCGYCTTATC MGGCCTAC        38

( 2 ) INFORMATION FOR SEQ ID NO:4:

( i ) SEQUENCE CHARACTERISTICS:
        ( A ) LENGTH: 18 base pairs
        ( B ) TYPE: nucleic acid (C) STRANDEDNESS: single
        (D) TOPOLOGY: linear (ii) MOLECULE TYPE: DNA (genomic)

(iii) HYPOTHETICAL: YES (ix) FEATURE:
        (A) OTHER INFORMATION: /note=N ="Inosine"

(xi) SEQUENCE DESCRIPTION: SEQ ID NO:4:

NNNNCGNCGN CATCNGGC　　　　　　　　　　　　　　　　　　　　　　　　　　　　　　　　18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) OTHER INFORMATION: /note="N =Inosine at position #
            N =A, G, C or T at position #

(xi) SEQUENCE DESCRIPTION: SEQ ID NO:5:

NNNRCGYCGN CATCMGGC　　　　　　　　　　　　　　　　　　　　　　　　　　　　　　　　18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) OTHER INFORMATION: /note="N =Inosine at position #
            N =A, G, C or T at position #

(xi) SEQUENCE DESCRIPTION: SEQ ID NO:6:

NNNNCGNCGN CATCNGGC　　　　　　　　　　　　　　　　　　　　　　　　　　　　　　　　18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) OTHER INFORMATION: /note="N =Inosine"

(xi) SEQUENCE DESCRIPTION: SEQ ID NO:7:

NCGNCTTATC NGGCCTAC　　　　　　　　　　　　　　　　　　　　　　　　　　　　　　　　18

(2) INFORMATION FOR SEQ ID NO:8:

(i) SEQUENCE CHARACTERISTICS:

(A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO:8:

RCGYCTTATC MGGCCTAC                                                                         18

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) FEATURE:
            (A) OTHER INFORMATION: /note="N =A, G, C or T"

(xi) SEQUENCE DESCRIPTION: SEQ ID NO:9:

NCGNCTTATC NGGCCTAC                                                                         18

(2) INFORMATION FOR SEQ ID NO:10:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) FEATURE:
            (A) OTHER INFORMATION: /note="N =Inosine"

(xi) SEQUENCE DESCRIPTION: SEQ ID NO:10:

GNCATCNGGC                                                                                  10

(2) INFORMATION FOR SEQ ID NO:11:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (ix) FEATURE:
            (A) OTHER INFORMATION: /note="N =A, G, C or T"

(xi) SEQUENCE DESCRIPTION: SEQ ID NO:11:

GNCATCMGGC                                                                                  10

(2) INFORMATION FOR SEQ ID NO:12:

(i) SEQUENCE CHARACTERISTICS:
            (A) LENGTH: 10 base pairs
            (B) TYPE: nucleic acid
            (C) STRANDEDNESS: single ( D ) TOPOLOGY: linear ( i i ) MOLECULE TYPE: DNA (genomic)

( i i i ) HYPOTHETICAL: YES ( i x ) FEATURE:
            ( A ) OTHER INFORMATION: /note="N =A, G, C or T"

( x i ) SEQUENCE DESCRIPTION: SEQ ID NO:12:

GNCATCNGGC                                                                                        10

( 2 ) INFORMATION FOR SEQ ID NO:13:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( i x ) FEATURE:
                ( A ) OTHER INFORMATION: /note="N =Inosine"

( x i ) SEQUENCE DESCRIPTION: SEQ ID NO:13:

NCGNCATCNG GC                                                                                     12

( 2 ) INFORMATION FOR SEQ ID NO:14:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( i x ) FEATURE:
                ( A ) OTHER INFORMATION: /note="N =A, G, C or T"

( x i ) SEQUENCE DESCRIPTION: SEQ ID NO:14:

YCGNCATCMG GC                                                                                     12

( 2 ) INFORMATION FOR SEQ ID NO:15:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( i x ) FEATURE:
                ( A ) OTHER INFORMATION: /note="N =A, G, C or T"

( x i ) SEQUENCE DESCRIPTION: SEQ ID NO:15:

NCGNCATCNG GC                                                                                     12

( 2 ) INFORMATION FOR SEQ ID NO:16:

( i ) SEQUENCE CHARACTERISTICS:
                ( A ) LENGTH: 24 base pairs
                ( B ) TYPE: nucleic acid
                ( C ) STRANDEDNESS: single ( D ) TOPOLOGY: linear ( i i ) MOLECULE TYPE: DNA (genomic)

( i i i ) HYPOTHETICAL: YES ( i x ) FEATURE:
    ( A ) OTHER INFORMATION: /note="N =Inosine"

( x i ) SEQUENCE DESCRIPTION: SEQ ID NO:16:

NCGNNNNNN CGNCGNCATC NGGC      24

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine"

( x i ) SEQUENCE DESCRIPTION: SEQ ID NO:17:

RCGYNNNNR CGYCGNCATC MGGC      24

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine at position #
        N =A, G, C or T at position #

( x i ) SEQUENCE DESCRIPTION: SEQ ID NO:18:

NCGNNNNNN CGNCGNCATC NGGC      24

( 2 ) INFORMATION FOR SEQ ID NO:19:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine"

( x i ) SEQUENCE DESCRIPTION: SEQ ID NO:19:

ATAAGNCGNN NNNNCGNCG NCATCNGGC      29

( 2 ) INFORMATION FOR SEQ ID NO:20:

( i ) SEQUENCE CHARACTERISTICS:
        ( A ) LENGTH: 29 base pairs
        ( B ) TYPE: nucleic acid (C) STRANDEDNESS: single
(D) TOPOLOGY: linear (ii) MOLECULE TYPE: DNA (genomic)

(iii) HYPOTHETICAL: YES (ix) FEATURE:
(A) OTHER INFORMATION: /note="N =Inosine"

(xi) SEQUENCE DESCRIPTION: SEQ ID NO:20:

ATAAGRCGYN NNNNRCGYCG NCATCMGGC 29

(2) INFORMATION FOR SEQ ID NO:21:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (ix) FEATURE:
(A) OTHER INFORMATION: /note="N =Inosine at position #
N =A, G, C or T position #

(xi) SEQUENCE DESCRIPTION: SEQ ID NO:21:

ATAAGNCGNN NNNNCGNCG NCATCNGGC 29

(2) INFORMATION FOR SEQ ID NO:22:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (ix) FEATURE:
(A) OTHER INFORMATION: /note="N =Inosine"

(xi) SEQUENCE DESCRIPTION: SEQ ID NO:22:

TCNGGCCTAC 10

(2) INFORMATION FOR SEQ ID NO:23:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (xi) SEQUENCE DESCRIPTION: SEQ ID NO:23:

TCMGGCCTAC 10

(2) INFORMATION FOR SEQ ID NO:24:

(i) SEQUENCE CHARACTERISTICS:
(A) LENGTH: 10 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: YES (i x) FEATURE:
    (A) OTHER INFORMATION: /note="N =A, G, C or T"

(x i) SEQUENCE DESCRIPTION: SEQ ID NO:24:

TCNGGCCTAC    10

(2) INFORMATION FOR SEQ ID NO:25:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (i x) FEATURE:
        (A) OTHER INFORMATION: /note="N =Inosine"

(x i) SEQUENCE DESCRIPTION: SEQ ID NO:25:

TATCNGGCCT AC    12

(2) INFORMATION FOR SEQ ID NO:26:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (x i) SEQUENCE DESCRIPTION: SEQ ID NO:26:

TATCMGGCCT AC    12

(2) INFORMATION FOR SEQ ID NO:27:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (i x) FEATURE:
        (A) OTHER INFORMATION: /note="N =A, G, C or T"

(x i) SEQUENCE DESCRIPTION: SEQ ID NO:27:

TATCNGGCCT AC    12

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(  i i i  ) HYPOTHETICAL: YES (  i x  ) FEATURE:
            ( A ) OTHER INFORMATION: /note="N =Inosine"

( x i ) SEQUENCE DESCRIPTION: SEQ ID NO:28:

NNNNNNCGN CTTATCNGGC CTAC					24

( 2 ) INFORMATION FOR SEQ ID NO:29:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: YES ( i x ) FEATURE:
            ( A ) OTHER INFORMATION: /note="N =Inosine"

( x i ) SEQUENCE DESCRIPTION: SEQ ID NO:29:

YNNNNNRCGY CTTATCMGGC CTAC					24

( 2 ) INFORMATION FOR SEQ ID NO:30:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: YES ( i x ) FEATURE:
            ( A ) OTHER INFORMATION: /note="N =Inosine at position #
                N =A, G, C or T at position #

( x i ) SEQUENCE DESCRIPTION: SEQ ID NO:30:

NNNNNNCGN CTTATCNGGC CTAC					24

( 2 ) INFORMATION FOR SEQ ID NO:31:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: YES ( i x ) FEATURE:
            ( A ) OTHER INFORMATION: /note="N =Inosine"

( x i ) SEQUENCE DESCRIPTION: SEQ ID NO:31:

CGNCGNNNNN NNCGNCTTAT CNGGCCTAC					29

( 2 ) INFORMATION FOR SEQ ID NO:32:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: DNA (genomic)

(  i i i  ) HYPOTHETICAL: YES (  i x  ) FEATURE:
    ( A ) OTHER INFORMATION: /note="N =Inosine"

(  x i  ) SEQUENCE DESCRIPTION: SEQ ID NO:32:

CGRCGYNNNN NRCGYCTTAT CMGGCCTAC 29

( 2 ) INFORMATION FOR SEQ ID NO:33:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine at position #
        N =A, G, C or T a position #

( x i ) SEQUENCE DESCRIPTION: SEQ ID NO:33:

CGNCGNNNNN NNCGNCTTAT CNGGCCTAC 29

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =Inosine"

( x i ) SEQUENCE DESCRIPTION: SEQ ID NO:34:

NNNNACGCCG CATCCGGC 18

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:35:

TCGGCTTATC GGGCCTAC 18

( 2 ) INFORMATION FOR SEQ ID NO:36:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: YES ( i x ) FEATURE:
   ( A ) OTHER INFORMATION: /note="N =A, G, C or T"

( x i ) SEQUENCE DESCRIPTION: SEQ ID NO:36:

TATACMCWAA ATMATTCGRG TTGCAKSAAG GCGGCAASNK AGTGAATYCC CRGGAGCWTA 60

SATAASTAWG TGACTGGGRT GARCRARCGM AGCCAACGCA SMTGCRRYYY GAARKAYGAM 120

GRGKAT 126

( 2 ) INFORMATION FOR SEQ ID NO:37:

( i ) SEQUENCE CHARACTERISTICS:
       ( A ) LENGTH: 126 base pairs
       ( B ) TYPE: nucleic acid
       ( C ) STRANDEDNESS: double
       ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:37:

TATACCCAAA ATAATTCGAG TTGCAGCAAG GCGGCAAGTG AGTGAATCCC CAGGAGCTTA 60

CATAAGTAAG TGACTGGGGT GAGCGAACGC AGCCAACGCA GCTGCAGCTT GAAATATGAC 120

GGGTAT 126

( 2 ) INFORMATION FOR SEQ ID NO:38:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:38:

ATGTAAGCTC CTGGGGATTC AC 22

( 2 ) INFORMATION FOR SEQ ID NO:39:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: YES ( i x ) FEATURE:
       ( A ) OTHER INFORMATION: /note="N =Inosine"

( x i ) SEQUENCE DESCRIPTION: SEQ ID NO:39:

ATNTANGCTC CNGGGNATTC AC 22

( 2 ) INFORMATION FOR SEQ ID NO:40:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: DNA (genomic)

(i i i) HYPOTHETICAL: YES (x i) SEQUENCE DESCRIPTION: SEQ ID NO:40:

ATSTAWGCTC CYGGGRATTC AC    22

(2) INFORMATION FOR SEQ ID NO:41:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: YES (i x) FEATURE:
      (A) OTHER INFORMATION: /note="N =A, G, C or T"

(x i) SEQUENCE DESCRIPTION: SEQ ID NO:41:

ATNTANGCTC CNGGGNATTC AC    22

(2) INFORMATION FOR SEQ ID NO:42:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: YES (x i) SEQUENCE DESCRIPTION: SEQ ID NO:42:

AAGTAAGTGA CTGGGGTGAG CG    22

(2) INFORMATION FOR SEQ ID NO:43:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: YES (i x) FEATURE:
      (A) OTHER INFORMATION: /note="N =Inosine"

(x i) SEQUENCE DESCRIPTION: SEQ ID NO:43:

AANTANGTGA CTGGGNTGAN C    21

(2) INFORMATION FOR SEQ ID NO:44:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: YES (x i) SEQUENCE DESCRIPTION: SEQ ID NO:44:

AASTAWGTGA CTGGGRTGAR C    21

(2) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =A, G, C or T"

( x i ) SEQUENCE DESCRIPTION: SEQ ID NO:45:

```
AANTANGTGA CTGGGNTGAN C                                        21
```

(2) INFORMATION FOR SEQ ID NO:46:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: YES ( i x ) FEATURE:
        ( A ) OTHER INFORMATION: /note="N =A, G, C or T at all
        locations; and at location 8 the N can be omitted to
        form a 26 mer sequence"

( x i ) SEQUENCE DESCRIPTION: SEQ ID NO:46:

```
GTNCNGNNTT TTTGTTAATN CNCTATA                                  27
```

(2) INFORMATION FOR SEQ ID NO:47:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:47:

```
GTACCGGTTT TTGTTAATTC ACTATA                                   26
```

(2) INFORMATION FOR SEQ ID NO:48:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:48:

```
ACAAAAACCG GTAC                                                14
```

(2) INFORMATION FOR SEQ ID NO:49:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: YES ( i x ) FEATURE:
  ( A ) OTHER INFORMATION: /note="N =Inosine"

( x i ) SEQUENCE DESCRIPTION: SEQ ID NO:49:

ACAAAAANCN GNAC 14

( 2 ) INFORMATION FOR SEQ ID NO:50:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:50:

ACAAAAAYCR GKAC 14

( 2 ) INFORMATION FOR SEQ ID NO:51:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: YES ( i x ) FEATURE:
    ( A ) OTHER INFORMATION: /note="N =A, G, C or T"

( x i ) SEQUENCE DESCRIPTION: SEQ ID NO:51:

ACAAAAANCN GNAC 14

( 2 ) INFORMATION FOR SEQ ID NO:52:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:52:

GTTAATTCAC TATA 14

( 2 ) INFORMATION FOR SEQ ID NO:53:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear (i i) MOLECULE TYPE: DNA (genomic)

(i i i) HYPOTHETICAL: YES (i x) FEATURE:
    (A) OTHER INFORMATION: /note="N =Inosine"

(x i) SEQUENCE DESCRIPTION: SEQ ID NO:53:

GTTAATNCNC TATA    14

(2) INFORMATION FOR SEQ ID NO:54:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (x i) SEQUENCE DESCRIPTION: SEQ ID NO:54:

GTTAATYCRC TATA    14

(2) INFORMATION FOR SEQ ID NO:55:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (i x) FEATURE:
        (A) OTHER INFORMATION: /note="N =A, G, C or T"

(x i) SEQUENCE DESCRIPTION: SEQ ID NO:55:

GTTAATNCNC TATA    14

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (x i) SEQUENCE DESCRIPTION: SEQ ID NO:56:

CGAGCTGTCC CAGTCCGC    18

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: YES (x i) SEQUENCE DESCRIPTION: SEQ ID NO:57:

```
GCGGACTGGG ACAGCTCG                                                                             18
```

( 2 ) INFORMATION FOR SEQ ID NO:58:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:58:

```
CAGCCATGAA CAACTGGTGG CG                                                                        22
```

( 2 ) INFORMATION FOR SEQ ID NO:59:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:59:

```
TGCTTTGCGC AGGGAAGATT CC                                                                        22
```

( 2 ) INFORMATION FOR SEQ ID NO:60:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:60:

```
YTAGAGYATT TGMCAAAAAG ACGCAACGTC TTTTTGGCGR GCGGACTGGG ACAGCTCGMA    60

GAGRGCGAGT GCAAAACACK GAGCAGGGCG                                    90
```

FINGERPRINTING BACTERIAL STRAINS USING REPETITIVE DNA SEQUENCE AMPLIFICATION

This application is a continuation of application Ser. No. 07/781,424 filed Oct. 23, 1991, now abandoned.

FIELD OF THE INVENTION

The present invention relates generally to the use of oligonucleotide probes directed to repetitive DNA sequence elements to identify bacteria. More particularly, it relates to the use of these probes as primers for the amplification of bacterial genomic DNA between repetitive sequences, and the use of these amplification products to construct DNA fingerprints unique to the probed genome. It also relates to the disclosure of specific primers which are useful as oligonucleotide probes in the practice of this invention.

BACKGROUND OF THE INVENTION

Interspersed repetitive DNA sequence elements have been characterized extensively in eucaryotes although their function still remains largely unknown. The conserved nature and interspersed distribution of these repetitive sequences have been exploited to amplify unique sequences between repetitive sequences by the polymerase chain reaction. Additionally, species-specific repetitive DNA elements have been used to differentiate between closely related murine species.

Prokaryotic genomes are much smaller than the genomes of mammalian species (approximately $10^6$ versus $10^9$ base pairs of DNA, respectively). Since these smaller prokaryotic genomes are maintained through selective pressures for rapid DNA replication and cell reproduction the non-coding repetitive DNA should be kept to a minimum unless maintained by other selective forces. For the most part prokaryotes have a high density of transcribed sequences. Nevertheless, families of short intergenic repeated sequences occur in bacteria.

The presence of repetitive sequences has been demonstrated in many different bacterial species. Reports of novel repeated sequences in the eubacterial genera, Escherichia, Salmonella, Deinococcus, Calothrix, and Neisseria, and the fungi, *Candida albicans* and *Pneumocystis carinii*, illustrate the presence of dispersed extragenic repetitive sequences in many organisms. One such family of repetitive DNA sequences in eubacteria is the Repetitive Extragenic Palindromic (REP) elements. The consensus REP sequence for this family includes a 38 mer sequence containing six totally degenerate positions, including a 5 bp variable loop between each side of the conserved stem of the palindrome. Another family of repetitive elements is the Enterobacterial Repetitive Intergenic Consensus (ERIC) sequences. ERIC is larger (consensus sequence is 126-mer) and contains a highly conserved central inverted repeat. The ERIC and REP consensus sequences do not appear to be related.

Previous studies have used repeated rRNA genes as probes in Southern blots to detect restriction fragment length polymorphisms (RFLPs) between strains. Repeated tRNA genes have been used as consensus primer binding sites to directly amplify DNA fragments of different sizes by PCR amplification of different strains. Limitations of both techniques include the use of radioisotope and time-intensive methods such as Southern blotting and polyacrylamide gel electrophoresis to clearly distinguish subtle differences in the sizes of the DNA fragments generated. The latter technique could only distinguish organisms at the species and genus level. The tDNA-PCR fingerprints are generally invariant between strains of a given species and between related species. Other previous studies include the use of species-specific repetitive DNA elements as primer-binding sites for PCR-based bacterial species identification. Though such methods allow species identification by PCR with picogram amounts of DNA, only single PCR products are generated which precludes the generation of strain-specific genomic fingerprints.

Although these previous studies demonstrated that species-specific repetitive DNA elements can be used as primer-binding sites for PCR-based bacterial species identification, these methods only generated single PCR products in a single species. The present invention provides a novel approach to using extragenic repetitive sequences to directly fingerprint bacterial genomes. Analysis of amplification products resulting from amplifying unique sequences between primers to bacterial DNA repeat sequences, reveals unique distances between repeat sequences. This pattern of distances uniquely fingerprints different bacterial species and strains. Thus, this approach provides a quick and reliable method to type bacteria by genomic fingerprinting.

SUMMARY OF THE INVENTION

An object of the present invention is a method of identifying a strain of bacteria by amplifying the DNA between repetitive DNA sequences and measuring the pattern of sized extension products.

An additional object of the present invention is provision of primer pairs to bacterial repetitive DNA sequences.

A further object of the present invention is a method of identifying a strain of bacteria in samples from physiological and non-physiological sources.

An additional object of the present invention is a method for diagnosing bacterial disease in humans and animals.

A further object of the present invention is the detection of bacterial disease or contamination in plants.

An additional object of the present invention is the monitoring of bacterial contamination in foods.

A further object of the present invention is a method for developing a library of fingerprints to identify specific strains of bacteria.

An additional object of the present invention is a method for monitoring bacterial contamination in soils, liquids, solids and other samples from environmental sources.

A further object of the present invention is a method for monitoring manufacturing processes for bacterial contamination.

An additional object of the present invention is a method for quality assurance or quality control of microbiological based laboratory assays.

A further object of the present invention is a method for genomic mapping.

An additional object of the present invention is the monitoring of bacterial populations in bioremediation sites.

A further object of the present invention is the monitoring of bacterial infections.

An additional object of the present invention is a method for the automated identification of a bacterial strain.

A further object of the present invention is a machine for the automated identification of bacterial strains.

Thus, in accomplishing the foregoing objects, there is provided in accordance with one aspect of the present invention a method for identifying a strain of bacteria in a sample, comprising the steps of: amplifying DNA between repetitive sequences in the bacteria by adding a pair of outwardly-directed primers to the sample, which primers are capable of hybridizing to repetitive DNA sequences in the bacterial DNA, and extending outwardly from one hybridizable repetitive sequence to another hybridizable repetitive sequence; separating the extension products generated in the amplification step by size; and determining the specific strain of bacteria by measuring the pattern of sized extension products.

In specific embodiments of the present invention the primers are between about 10 to 29 mer and preferably between about 15 to 25 mer.

The primers can be specific to any repetitive sequence but in the preferred embodiments are specific to ERIC, REP, Ngrep or Drrep.

In various aspects of the present invention the method can be used for: (1) diagnosis of bacterial disease, in plants animals and humans; (2) monitoring for bacterial content and/or contamination in the environment; (3) monitoring food for bacterial contamination; (4) monitoring manufacturing processes for bacterial contamination; (5) monitoring quality assurance/quality control of laboratory tests involving microbiological assays; (6) tracing bacterial contamination and/or outbreaks of bacterial infections; (7) genome mapping; (8) monitoring bioremediation sites; and (9) monitoring agricultural sites for test crops, bacteria and recombinant molecules.

The method is useful on pure or isolated cultures as well as actual samples from the test site. In a preferred embodiment multiple primers to different repetitive DNA can be used.

Because of the simplicity of the test it can also be automated for rapid and quick assay of samples.

A further aspect of the present invention is a machine for automating the identification of bacterial strains.

Other and further objects, features and advantages will be apparent from the following description of the presently preferred embodiments of the invention, which are given for the purpose of disclosure, when taken in conjunction with the accompanying drawings.

DESCRIPTION OF THE DRAWINGS

FIG. 8 shows a "bug blot" hybridization of REP in a wide variety of bacteria.

FIG. 10 shows a "bug blot" hybridization of ERIC in a wide variety of bacteria.

Figure 1:
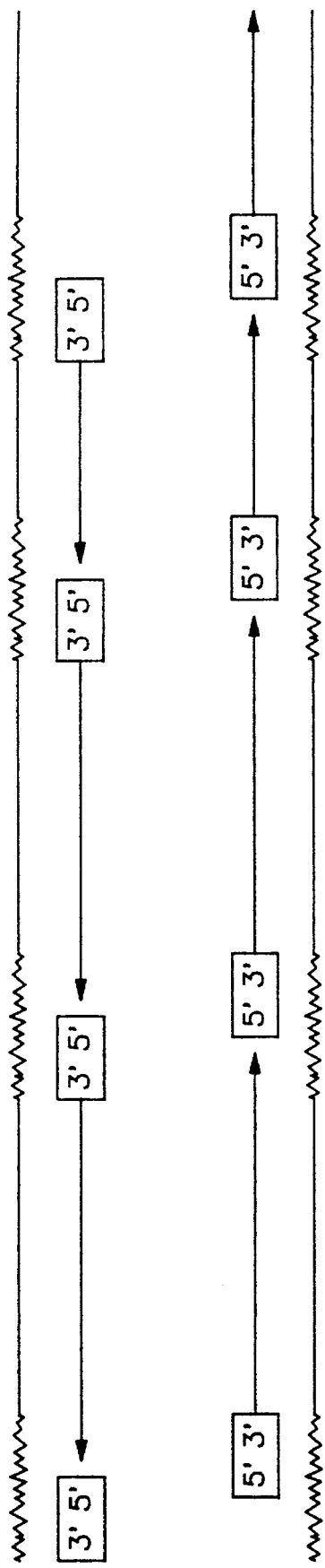
FIG. 1 is a schematic showing the binding of outwardly-directed primers.

Drawings are not necessarily to scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

DNA amplification as used herein refers to any process which increases the number of copies of a specific DNA sequence. A variety of processes are known. One of the most commonly used is the Polymerase Chain Reaction (PCR) process of Mullis as described in U.S. Pat. Nos. 4,683,195 and 4,683,202 both issued on Jul. 28, 1987. In general the PCR amplification process involves an enzymatic chain reaction for preparing exponential quantities of a specific nucleic acid sequence. It requires a small amount of a sequence to initiate the chain reaction and oligonucleotide primers which will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed. In the present invention the extension product traverses from one repetitive sequence to another repetitive sequence. Since the repetitive sequences are interspersed throughout the genome at different distances from each other, there will be exponential growth of all the different sizes. The pattern of extension products of different sizes provides a specific fingerprint for each bacteria.

The term "oligonucleotide primer" as used herein defines a molecule comprised of more than three deoxyribonucleotides or oligonucleotides. Its exact length will depend on many factors relating to the ultimate function and use of the oligonucleotide primer, including temperature, source of the primer and use of the method. The oligonucleotide primer can occur naturally (as a purified fragment or restriction digestion product) or be produced synthetically. The oligonucleotide primer is capable of acting as an initiation point for synthesis, when placed under conditions which induce synthesis of a primer extension product complementary to a nucleic acid strand. The conditions can include the presence of nucleotides and an inducing agent such as a DNA polymerase at a suitable temperature and pH. In the preferred embodiment the primer is a single-stranded oligodeoxyribonucleotide of sufficient length to prime the synthesis of an extension product from a specific sequence in the presence of an inducing agent. In the present application in the preferred embodiment the oligonucleotides are usually between about 10 mer and 29 mer. In the preferred embodiment they are between 15 and 25 mer. Sensitivity and specificity of the oligonucleotide primers are determined by the primer length and uniqueness of sequence within a given sample of a template DNA. Primers which are too short, for example, less than 10 mer may show non-specific binding to a wide variety of sequences in the genomic DNA and thus are not very helpful.

Each primer pair herein is selected to be substantially complementary to the different strands of each specific repetitive sequence to which the primer pairs bind. Thus one primer of each pair is sufficiently complementary to hybridize with a part of the sequence in the sense strand and the other primer of each pair is sufficiently complementary to hybridize with a different part of the same repetitive sequence in the anti-sense strand.

It should also be recognized that a single primer can be considered a primer pair in this invention. Because the primer binds to repetitive sequences and because the repetitive sequences can be orientated in both directions, a single primer can bind to both strands of a repetitive sequence and amplify the sequence between two separate repetitive sequences.

As used herein the term "outwardly directed" primer pair refers to the oligonucleotide primers and their binding as seen in FIG. 1. In the present application one primer is substantially complementary to the sense strand. This primer binds to the sense strand in such an orientation that the extension product generated from the 3' end of the primer extends away from the repetitive DNA sequence to which the oligonucleotide primer is bound and across the non-repetitive DNA to a second repetitive DNA sequence. The other member of the primer pair binds to the antisense strand. This primer binds in an orientation such that extension products generated on the 3' end extends away from the repetitive DNA sequence to which the primer is bound and across the non-repetitive DNA to the next repetitive DNA sequence. Thus, within a specific repetitive DNA sequence the primer pair is bound to the complementary DNA strands 5' to 5' (see FIG. 1) and, thus, the extension products grow away from each other across the non-repetitive DNA. The extension products from the two paired primers are complementary to each other and can serve as templates for further synthesis by binding the other member of the primer pair.

As used herein the term "extension product" refers to the nucleotide sequence which is synthesized in the presence of nucleotides and an inducing agent such as a polymerase from the 3' end of the oligonucleotide primer and which is complementary to the strand to which the oligonucleotide primer is bound.

As used herein the term "differentially labelled" shall indicate that the extension product can be distinguished from all the others because it has a different label attached or is of a different size or binds to a specific oligonucleotide or a combination thereof. One skilled in the art will recognize that a variety of labels are available. For example, these can include radioisotopes, fluorescers, chemluminescers, enzymes and antibodies. Various factors affect the choice of the label. These include the effect of the label on the rate of hybridization and binding of the primer to the DNA, the sensitivity of the label, the ease in making the labeled primer, probe or extension products, the ability to automate, available instrumentation, convenience and the like. For example in one embodiment of the present invention size alone is sufficient to distinguish the patterns and thus no other label is needed. The size differences can be determined after staining the DNA, for example with ethidium bromide. However, when detecting multiple species in a sample or for multiple repetitive sequences it may be advantageous to add a radioactive label such as $^{32}P$, $^{3}H$ or $^{14}C$; a different fluorescer such as fluorescein, tetramethylrhodamine, Texas Red or 4-chloro-7-nitrobenzo-2-oxa-1-diazole (NBD); or a mixture of different labels such as radioisotopes, fluorescers and chemluminescers.

The term "repetitive DNA" as used herein refers to non-coding sequences of DNA containing short repeated sequences and dispersed throughout the bacterial genome.

As used herein (1) "REP" refers to the repetitive extragenic palindromic elements. The REP consensus sequence is shown in SEQ. ID. NO. 1. (2) "ERIC" refers to the enterobacterial repetitive intergenic consensus sequence. The ERIC consensus sequence is shown in SEQ. ID. NO. 36. (3) "Ngrep" refers to the Neisseria repetitive elements. The Ngrep consensus sequence is shown in SEQ. ID. NO. 46. (4) "Drrep" refers to the Deinococcus repetitive elements. The Drrep consensus sequence is shown in SEQ. ID. NO. 60. These repetitive elements are found interspersed throughout the bacterial genome. These four sequences or any combination of these four sequences can be used in the present invention. Further, one skilled in the art will understand that as new repetitive sequences in bacteria become known they can also be used in the method of the present invention. By binding outwardly-directed primers to these repetitive sequences and performing amplification one can generate unique fingerprints and identify individual strains of bacteria.

The oligonucleotide primers may be prepared using any suitable method known in the art. For example the phosphodiester, and phosphotriester methods or automated embodiments thereof. It is also possible to use a primer which has been isolated from biological sources such as with a restriction endonuclease digest.

The repetitive sequence to which the primers bind can be selected from any of the repetitive regions that are found in bacteria. The repetitive sequences can be identified by a variety of methods. This may be done manually by comparing the sequences of the published nucleic acid sequences for bacterial genomes. A more convenient method, however, is to use a computer program to compare the sequences. In this way one can generate a consensus DNA sequence for use in the methods of the present application.

Any source of bacterial nucleic acid in purified or non-purified form can be utilized as starting material, provided it contains or is suspected of containing a bacterial genome of interest. Thus, the bacterial nucleic acids may be obtained from any source which can be contaminated by bacteria. When looking for bacterial infection or in distinguishing bacteria from human or animal subjects, the sample to be tested can be selected or extracted from any bodily sample such as blood, urine, spinal fluid, tissue, vaginal swab, stool, amniotic fluid or buccal mouthwash.

In other applications the sample can come from a variety of sources. For example: (1) in horticulture and agricultural testing the sample can be a plant, fertilizer, soil, liquid or other horticultural or agricultural product; (2) in food testing the sample can be fresh food or processed food (for example infant formula, seafood, fresh produce and packaged food); (3) in environmental testing the sample can be liquid, soil, sewage treatment, sludge and any other sample in the environment which is considered or suspected of being contaminated by bacteria.

When the sample is a mixture of material for example blood, soil and sludge it can be treated within an appropriate reagent which is effective to open the cells and expose or separate the strands of nucleic acids. Although not necessary, this lysing and nucleic acid denaturing step will allow amplification to occur more readily. Further, if desired, the bacteria can be cultured prior to analysis and thus a pure sample obtained. This is not necessary, however.

The inducing agent for polymerization may be any compound or system which will function to accomplish the synthesis of primer extension products. Examples of inducing enzymes which have been used for this purpose include E. coli DNA polymerase I, Klenow fragment of E. coli DNA polymerase I, T4 DNA polymerase, Taq DNA polymerase, Vent DNA polymerase and other available DNA polymerases.

As used herein "fingerprinting" refers to the fact that each strain of bacteria has its characteristic size pattern of extension products which can be used to identify the bacterial strain. This unique pattern is each strain's genomic fingerprint.

One embodiment of the present invention includes a method for identifying a strain of bacteria in a sample, comprising the steps of: amplifying DNA by adding a pair of outwardly-directed primers to the sample, wherein the primers are capable of hybridizing to repetitive DNA sequences in the bacterial DNA and extending outwardly from one hybridizable repetitive sequence to another hybridizable repetitive sequence; separating the extension products generated in the amplification step by size; and determining the specific strain of bacteria by measuring the pattern of sized extension products.

It will be recognized that the separating step of this embodiment may be accomplished by any number of techniques and methods which will separate the extension products by size. Examples include but are not limited to gel electrophoresis, capillary electrophoresis, chromatography, pulsed field gel electrophoresis and mass spectrometry. Thus, one skilled in the art will recognize that the separation of extension products can be done by a variety of methods. The choice of method will depend on a number of factors, such as the available laboratory equipment, the amount of extension product present, the label if any, the dye, the preference of the party performing the testing, convenience and the like.

Capillary electrophoresis allows the rapid separation of DNA fragments through tiny polyacrylamide gels in thin capillaries. The chief advantage is that much larger voltages can be applied and resolution is enhanced. The process can be automated. Once tubes are loaded, electrophoresis and data acquisition can be automated by direct connection to computer. An example includes the Model 270A-HT High Throughput Capillary Electrophoresis System (Applied Biosystems). Instead of bands on a gel, the DNA fragments are represented by spikes as a function of time indicating the presence of different molecules of different sizes. Another advantage is that not only can PCR-generated spike patterns be quickly obtained with greater resolution of different-sized fragments, but intensity of different bands could be accurately quantitated; permitting even greater resolution.

Non-electrophoresis methods, namely chromatography, can be used to separate PCR-generated DNA fragments by size. High-Performance Liquid Chromatography (HPLC) methods can be used to separate DNA fragments by the use of size-exclusion columns (Series 800 HRLC Gradient System—BioRad). DNA fragments are represented by spikes as a function of time and the data is digitized and fed directly to a computer. Electrophoresis methods, however, are usually preferred because of greater reliability and resolution.

One skilled in the art will recognize that measurement of the pattern of sized extension products to determine the specific strain of bacteria present may also be accomplished by several means, direct visualization or by automation using a bar code reader, a laser reader, digitizer, a photometer, a fluorescence reader or computer planimetry. The choice of measurement method depends in part on the separation step and available instrumentation.

A variety of primers can be used to detect repetitive sequences in bacteria. The primers depend on which repetitive sequence is being detected and which bacteria are being detected. One skilled in the art can readily determine which repetitive sequence and primers to use depending on the bacteria being examined. In the embodiment of the present invention primer pairs have been selected from the sequences in the groups consisting of SEQ. ID. NOS. 4 to 35, 38 to 45 and 48 to 57. In the preferred embodiment when REP is being used for the primer annealing site one member of the pair of primers is selected from the group consisting of SEQ. ID. NOS. 4, 5, 6, 10, 11, 12, 13, 14, 15, 16, 17, 18, 19, 20, 21 and 34 and the other member of the pair is selected from the group consisting of SEQ. ID. NO. 7, 8, 9, 22, 23, 24, 25, 26, 27, 28, 29, 30, 31, 32, 33, and 35. In the most preferred embodiment SEQ. ID. NO. 4 and SEQ. ID. NO. 7 are used.

When the repetitive sequence is ERIC one member of the pair of primers is selected from this group consisting of SEQ. ID. NO. 38, 39, 40, and 41 and the other member of the pair is selected from SEQ. ID. NOS. 42, 43, 44 and 45 and in the most preferred embodiment SEQ. ID. NO. 38 and SEQ. ID. NO. 42 are used.

When the repetitive sequence is Ngrep one member of the pair of primers is selected from the group consisting of SEQ. ID. NOS. 48, 49, 50 and 51 and the other member of the pair is selected from the group consisting of SEQ. ID. NOS. 52, 53, 54 and 55 In the preferred embodiment SEQ. ID. NO. 48 and SEQ. ID. NO. 52 are used.

When the repetitive sequence is Drrep only a single primer is used. The primer is either SEQ. ID. NOS. 56 or 57. This is an example where a single primer acts as a pair. Use of both primers will not result in unique fingerprint patterns.

One skilled in the art will readily recognize that as more repetitive sequences are determined the primer pair which gives the best fingerprint pattern can be easily selected. For example, a primer to the new sequence is synthesized and the method of the present invention is seen. After examining the resulting pattern from each primer pair the primer pair which best distinguishes the specific test strains can be identified.

In addition to the above described method a plurality of pairs of primers can be added to the method. Each pair of primers will bind a different repetitive sequence. For example, any combination of two or more of each of REP, ERIC, Ngrep and Drrep primer pairs can be added. Further, the multiprimer assay can be enhanced by differentially labeling the primer pairs. Thus, after amplification, not only can the sized pattern be examined, but the size pattern for each label can be examined. For example, REP and ERIC oligonucleotide primers can be used. Each is labeled with a different fluorescent label. The resultant differential labeling pattern can be determined by fluorescence scanning. This procedure can provide finer fingerprint patterns.

After electrophoresis in polyacrylamide gels, the gels are scanned by a laser-based fluorescence detector and the results digitized directly by computer connected to the detector. Further, using a Genescanner (Applied Biosystems) allows the entire process to be automated.

One skilled in the art will readily recognize that this method has many advantages. It can be readily modified for automated identification of strains of bacteria. In one embodiment the amplification is done in an auto-PCR instrument, the extension products are removed and separated on a sizing gel or by chromatography. The sizing pattern is determined by an automatic reader and each pattern can be recognized by a computer means. The computer will store fingerprints of known bacteria for comparison with test results. In the automated method, bar code readers, laser readers, digitizers, photometers, fluorescent readers and computer planimetry can be used to help automate the system.

In another embodiment of the present invention there is a kit for determining the identity of strains of bacteria. This kit comprises a container having a pair of outwardly-directed PCR primers to a repetitive sequence in bacteria. This kit can have any of the PCR primers selected from the group consisting of SEQ. ID. NO. 4 to 35, 38 to 45 and 48 to 57 or combination thereof. One skilled in the art will readily recognize that the number and type of primers which are in the kit will depend on the use of the kit as well as the sequences which are to be detected.

A further embodiment of the present invention is a machine for identifying a strain of bacteria comprising an automated PCR amplifying means, a separation means, a sampling means for removing the extension products from the PCR means and transferring them to the separation means, a reading means for measuring patterns of extension products after separation of the separation means, a computer means for recording the results of the reading means and for outputting the pattern of and identifying the strain of bacteria.

A number of automated PCR amplifying means are known on the market. For instance a thermal cycler can be used. There are a number of arms or robotic devices and other automatic pipette and sampling machines which can be used as a sampling means for removing the extension products from the PCR reaction at the appropriate times and transferring the sample for either chromatography, gel or capillary electrophoresis, mass spectrometry or other methods or techniques used to separate the samples. In the preferred embodiment the separator means is regulated by the computer. After the separation the reader means is used to measure the pattern. The reader means will depend on the type of separation which is being used. For instance a wavelength densitometer reader or a fluorescence reader can be used depending on the label being detected. A radioisotope detector can be used for radioisotope labeled primers. In mass spectrometry the ions are detected in the spectrometer. A gel can be stained and read with a densitometer. The computer regulates the automated PCR amplification procedure, the sampling and removal from PCR, the automatic separation and reading of the samples and can be used to interpret the results and output the data.

The methods, instruments and procedures described herein can be used for a variety of purposes. Because of the sensitivity and specificity of the test one skilled in the art will readily recognize uses for this methodology. What follows is not an inclusive list of uses but only a sampling of specific areas where a current need exists for a quick and reliable test.

The methodology of the present invention can be used for diagnosing bacterial diseases whether it is in plants, animals or humans. Not only can the disease be diagnosed but the specific strain involved can be identified.

The environment can be monitored for bacterial contamination. The procedure works on variety of samples including liquids, sludge, sewage treatment plant samples and soil. Thus, anywhere that there has been environmental contamination that needs monitoring, the test will work.

This procedure should be very useful in the area of monitoring food contamination. A variety of producers of foods currently test their products for bacterial contamination. This procedure will help facilitate this testing. For example infant formula, seafood, fresh produce and processed food can all be readily tested by this procedure. This procedure can also be useful to detect the source of food poisoning.

Another important use of this method is in the monitoring of the bacterial populations in a bioremediation site. Bioremediation usually uses specific bacterial populations to destroy the contamination. The bacteria can be from the natural population growing at the site or bacteria added to the site to enhance the breakdown. The bacteria used in the enhancement procedures usually are from cultures and/or sludge. In any of these instances it is important to monitor the population of bacteria in the bioremediation state to make sure that the appropriate strain(s) of bacteria is present and growing. This procedure allows the rapid and quick identification of the bacteria in the population so that it can be readily monitored. The test works on samples of soil, liquid, sludge or other material to be added to the bioremediation site.

In the areas of horticulture and agriculture a variety of uses of this method are found. One can monitor bacterial inoculations of plants or bacterial disease of plants. It can also be used to monitor the distribution of recombinant bacteria added to the environment. Samples can come from the soil where bacteria have been added, or from fertilizer to make sure that the fertilizer has the appropriate bacteria. It can be used to monitor pest control where bacteria are added in order to kill pests such as insects. This procedure allows quick and accurate monitoring of the application of the bacterial insecticide and the activity of the insecticide. Thus, in any horticulture or agriculture procedure which requires the addition of bacteria the bacteria can be monitored throughout the procedure.

Another application of this method is in the manufacturing process. A number of manufacturing processes for instance drugs, microorganism-aided synthesis, food manufacturing, chemical manufacturing and fermentation process all rely either on the presence or absence of bacteria. In either case the method of the present invention can be used. It can monitor bacterial contamination or test that strain purity is being maintained.

This method can also be used to test stored blood for bacterial contamination. This would be important in blood banking where bacteria such as *Yersinia enterocolitica* can cause serious infection and death if it is in transfused blood.

The procedure can also be used for quality assurance and quality control in monitoring bacterial contamination in laboratory tests. For example the Guthrie bacterial inhibition assay uses a specific strain of bacteria to measure phenylalanine in newborn screening. If this strain changes it could affect test results and thus affect the accuracy of the newborn screening program. This method of the present invention can be used to monitor the strain's purity. Any other laboratory test which uses or relies on bacteria in the assay can be monitored. The laboratory or test environment can also be monitored for bacterial contamination by sampling the lab and testing for specific strains of bacteria.

This procedure will also be useful in hospitals for tracing the origin and distribution of bacterial infections. It can show whether or not the infection of the patient is a hospital-specific strain. The type of treatment and specific anti-bacterial agent can depend on the source and nature of the bacteria.

The following examples are offered by way of example, and are not intended to limit the scope of the invention in any manner.

EXAMPLE 1

Isolation and Quantitation of Genomic DNA

1. Genomic DNA from Gram-negative and spirochete bacteria.

Cells were pelleted and washed twice in 1 ml of 1M NaCl by centrifugation in a fixed angle microfuge at 15,000 rpm for 5 min. Cells were washed twice and resuspended in TE (10 mm Tris, 25 mM EDTA, pH 8.0) and incubated in 0.2 mg/ml lysozyme and 0.3 mg/ml RNase A for 20 min at 37° C. If lysis by lysozyme was not visible with refractory pathogenic strains, 0.6% SDS was added. To these suspensions, 1% Sarkosyl and 0.6 mg/ml proteinase K were added, and the cells were incubated for 1 hr at 37° C. Cell lysates were extracted twice with phenol and twice with chloroform. The aqueous phase was precipitated with 0.33M $NH_4$ acetate and 2.5 volumes of ethanol. Precipitated threads of DNA were removed with a sterile Pasteur pipette tip, and dissolved in TE (10 mM Tris, 1 mM EDTA, pH 8.0).

2. Genomic DNA from Gram-positive bacteria.

Concentrated cell pellets were washed twice in 1M NaCl and twice in TE (50 mM Tris, 50 mM EDTA, pH 7.8) and spun in a fixed-angle microfuge for 5 min. Cell pellets were resuspended in TE and incubated with 250 U/ml mutanolysin and 0.3 mg/ml RNAse A for 30 min at 37° C. To this reaction, 0.6% SDS and 0.6 mg/ml proteinase K were added, and the mixture was incubated for 1 hr at 37° C., followed by 65° C. for 45 min. Lysates were extracted twice with phenol and twice with chloroform. Chromosomal DNA was precipitated and dissolved as described for Gram-negative bacteria.

In both instances the genomic DNA was quantitated by spectrofluorimetry at excitation and emission wavelengths of 365 nm and 460 nm respectively using the DNA-specific dye, Hoechst 33258 and a fluorometer.

EXAMPLE 2

Primer Synthesis

The oligonucleotide primers were synthesized by the phosphoramidite method using an automated DNA synthesizer, and DNA sequence information from consensus sequence data. The primers were labeled by 5' end-labeling of each oligonucleotide as described by Maniatis et al. Molecular cloning: A laboratory manual. Cold Spring Harbor Laboratory Press, Cold Spring Harbor, N.Y. (1982). Fifty pmol of each primer were used with 20 U T4 polynucleotide kinase and 5 µl of $\gamma^{-32}P$-ATP (6000 Ci/mmol).

Labeled DNA was separated from unincorporated isotope by diluting the 50 µl reaction volume to 1.0 ml in millipore water, followed by centrifugation of this solution through Centricon-3 (Amicon) tubes. The retained solution contains the hybridization probe. Oligonucleotides were quantitated by UV-VIS spectrophotometry with absorption measured at 260 nm.

EXAMPLE 3

Primer Design

1. REP oligonucleotide sequences are shown in SEQ. ID. NOS. 1 to 35 and FIG. 2. Degenerate 38-mer REPALL (SEQ. ID. NOS. 2 and 3) probes were designed which encompassed the entire consensus REP sequence (SEQ. ID. NO. 1). Other REP oligonucleotide probe pairs, each representing part of the conserved consensus sequence, were designed with opposite orientations such that the 3' ends were directed outwards from each REP sequence. This design constituted a pair of outwardly-directed primers. If the primer to one side of the sequence is shorter than the other, inosines may be added to make the lengths of the pair equal. Total degeneracy is represented either by any one of the four common bases (A, G, C, or T) placed at specific positions, or inosines placed at specific positions. Inosine contains the purine base, hypoxanthine, and is capable of forming Watson-Crick base pairs with A, G, C, or T. Positions can be partially degenerate with two of these four bases placed at specific positions as chosen from the consensus REP sequence.

Figure 3:
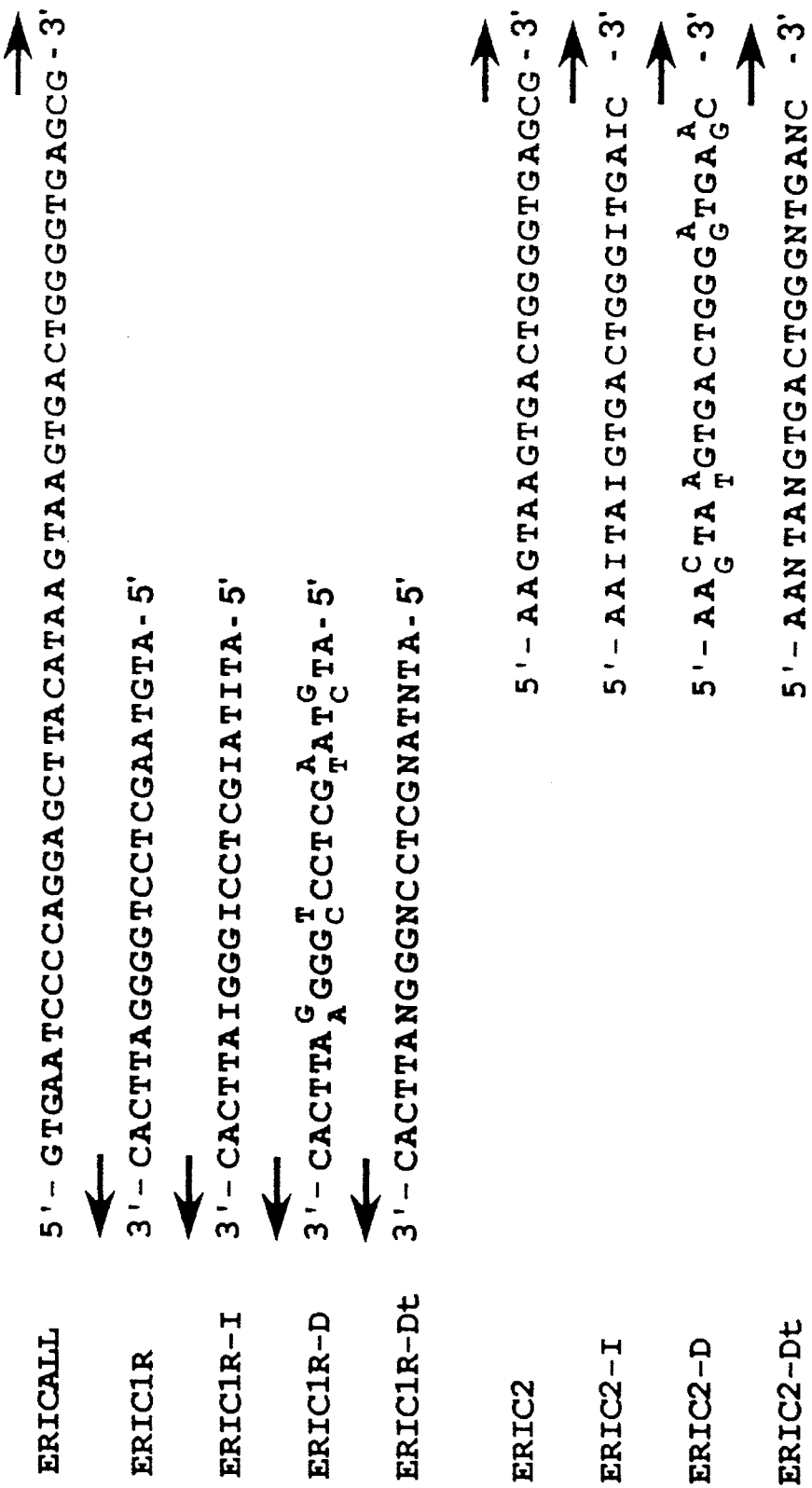
FIG. 3 shows the alignment of ERIC oligonucleotide primer sequences with respect to the central inverted repeat of an ERIC consensus sequence.

2. ERIC oligonucleotide sequences are shown in SEQ. ID. NOS. 36 to 45 and FIG. 3. The ERICALL oligonucleotide is a 44 mer of SEQ. ID. NO. 37 from position 42 to 85 and contains the entire conserved central core inverted repeat. Non-degenerate, consensus ERIC1R (SEQ. ID. NO. 38) and ERIC2 (SEQ. ID. NO. 42) oligonucleotides were designed from each half of this core inverted repeat with opposite orientations such that the 3' ends are directed outwards from the center of the ERIC element.

3. Ngrep sequences are shown in SEQ. ID. NOS. 46 to 55. SEQ. ID. NO. 46 is the consensus sequence.

4. Drrep sequences are shown in SEQ. ID. NOS. 56, 57 and 60. SEQ. ID. NO. 60 is the consensus sequence.

EXAMPLE 4

Membrane Supported Hybridization

A single membrane containing genomic DNA from 39 different eubacterial species representing 7 of 10 different phyla of eubacteria as defined by Woese, *Microbiol Rev.*, 51:221–271 (1987), based on rDNA sequence comparisons, was named the "bug blot." This bug blot was made by adding 100 ng of denatured genomic DNA per slot, from each species listed in FIGS. 8 or 10, on Gene Screen Plus (Du Pont) membranes. The bug blot represents a slot blot DNA:DNA hybridization of genomic DNA probed with $^{32}P$-end labeled SEQ. ID. NO. 3 (FIG. 8) or SEQ. ID. NO. 42 (FIG. 10). These membranes were pretreated as described in Maniatis et al. Genomic DNAs were denatured in solution by heating to 100° C. for 5 min. DNA samples were then applied to the membrane, and 500 µl 0.4N NaOH were added to each slot. Membranes were rinsed in 1× SSC, and blotted dry with Whatman paper. Membranes were baked at 80° C. for 1 hr, and stored in sealed plastic bags at −20° C.

The hybridization solution was prepared as described in Noda, A, et al. *Biotechniques* 10:474–477 (1991) for use with oligonucleotide probes on a membrane containing ordered lambda phages representing the *E. coli* W3110 genome. For REP oligonucleotide hybridization, membranes were prehybridized at 42° C. for 1.5 hrs. The probe was denatured at 100° C. for 5 min. Probe was added at $1\times10^6$ cpm/ml hybridization solution and the membranes were incubated at 42° C. for 15 hrs. ERIC oligonucleotide prehybridizations and hybridizations were both performed at 65° C. After incubation the membranes were washed twice at room temperature for 10 min with 2× SSPE and 0.1% SDS, followed by one final wash (REP, 37° C. for 15 min; ERIC, 40° for 1 min). Autoradiograms were exposed on Kodak X-Omat film with two intensifying screens at −85° C. for 24 hrs.

EXAMPLE 5

DNA Amplification

There are a number of DNA amplification methods available in the art. These generally depend on the use of one or more of a variety of polymerases to catalyze DNA chain extension (polymerization) from component nucleotide bases. An example of a DNA amplification technique is the polymerase chain reaction (PCR) used here to catalyze the extension of the oligonucleotide primer from the 3' end along the DNA template to which the primer is hybridized.

Each 25 μl of PCR reaction contained 50 pmol each of 2 opposing primers, 100 ng of template (genomic) DNA, 1.25 mM of each of 4 dNTPs, 2 U AmpliTaq DNA polymerase (Perkin-Elmer/Cetus) in a buffer with 10% DMSO (v/v). PCR amplifications were performed in an automated thermal cycler, with an initial denaturation at 95° C. for 7 min, followed by 30 cycles of denaturation at 90° C. for 30 sec., followed by annealing (REP, 40° C. for 1 min; ERIC, 52° C. for 1 min), and then extension (65° C. for 8 min), with a single final extension (65° C. for 16 min). All PCR reaction tubes were placed in internal rows of the thermal cycler and all peripheral tubes were surrounded by "dummy" tubes containing water and mineral oil. Five to eight μl of each PCR reaction volume were then electrophoresed directly on 1% agarose gels containing 1× TAE (Tris acetate-EDTA), and 0.5 μg/ml ethidium bromide. The gels were photographed with 20 second exposures to Polaroid type 55 film.

EXAMPLE 6

REP Primers

Figure 4:
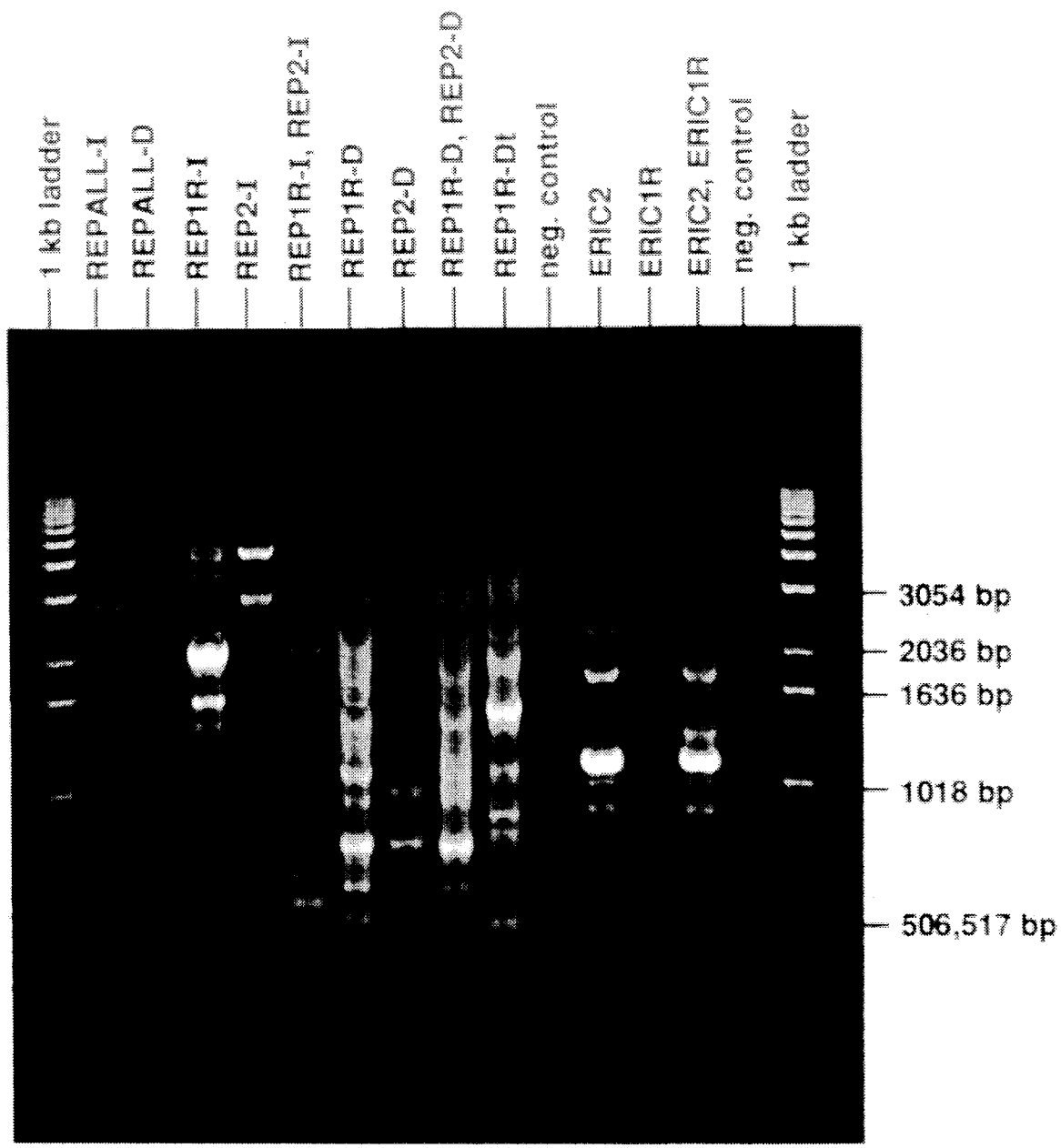
FIG. 4 shows PCR amplification of E. coli strain W3110 genomic DNA with different REP and ERIC oligonucleotide primer sets.

Genomic DNA from lysed *E. coli* W3110 cells served as the test sample. REP1R-I (SEQ. ID. NO. 4) and REP2-I (SEQ. ID. NO. 7) oligonucleotides were used as the pair of outwardly-directed primers. PCR amplification was accomplished as described above. Separation of amplification products was accomplished on 1% agarose—1× Tris-acetate-EDTA gel, and the pattern of sized extension products was determined using ethidium bromide to stain the DNA. No template DNA was added to the negative control lanes. REP1R-I and REP2-I primers were used in negative control lane 11. Results are shown in FIG. 4. The inosine-containing outwardly-directed primer pair, REP1R-I and REP2-I, provided the most distinct genomic fingerprint of *E. coli* strain W3110 chromosomal DNA. REP oligonucleotides (FIG. 2) were all tested as primers for DNA amplification because these outwardly-directed primers can amplify DNA between successive REP sequences in any orientation. The inosine-containing primer, however, provided more distinct DNA amplification band patterns and less smearing, possibly because each primer is represented by a single primer sequence instead of a pool of multiple primer sequences as with REP1R-D (SEQ. ID. NO. 5) and REP2-D (SEQ. ID. NO. 8). Each REP primer alone yielded visible amplification products of relatively limited complexity. This result probably stems from the fact that each side of the inverted repeat has a slightly different consensus sequence. The use of both primers REP1R-I and REP2-I appears to allow optimal annealing with both sides of the conserved stem of each REP-like sequence in the genome. Inefficient amplification with REPALL-I (SEQ. ID. NO. 2) and REPALL-D (SEQ. ID. NO. 3) was observed presumably because a palindrome is present in the primer. Because of the possible self-hybridization between REPALL primers of opposite orientation it was not possible to design the primers to the complete REP consensus sequence in both orientations.

EXAMPLE 7

ERIC Primers

Using genomic DNA from lysed *E. coli* W3110 cells as the test sample, ERIC1R (SEQ. ID. NO. 38) and ERIC2 (SEQ. ID. NO. 42) oligonucleotides were used as the pair of outwardly-directed primers. PCR amplification was accomplished as described above. Separation of amplification products was accomplished on 1% agarose—1× Tris-acetate-EDTA gel, and the pattern of sized extension products was determined using ethidium bromide to stain the DNA. No template DNA was added to the negative control lanes. ERIC1R and ERIC2 primers were used in negative control lane 15. Results are shown in FIG. 4. Amplification results obtained with the single consensus ERIC primer set, ERIC1R and ERIC2 (FIG. 4), were matched in complexity by the results obtained with ERIC2 alone (FIG. 4). In contrast PCR amplification with ERIC1R alone yielded limited amplification products (FIG. 4). Two possible reasons for this observation are that either greater sequence conservation exists in the side of the inverted repeat complementary to ERIC2 or homologous, unrelated sequences complementary to ERIC2 exist outside ERIC elements in the genome.

EXAMPLE 8

Specificity of Primer/Template Interactions.

Figure 5:
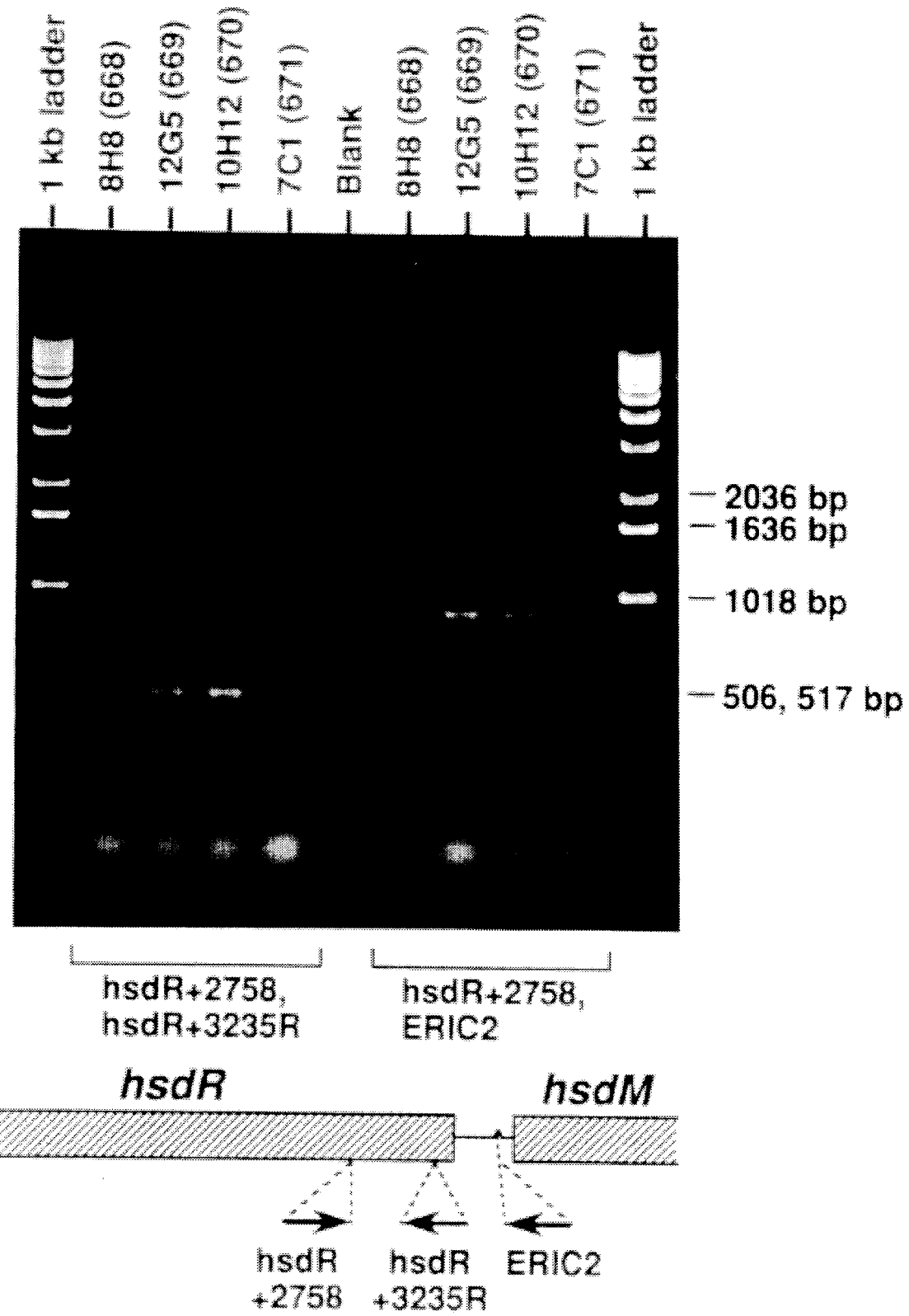
FIG. 5 is a 1% agarose gel demonstrating the specificity of ERIC oligonucleotide primer/template interactions.

PCR reactions using primer binding sites at known distances from ERIC sequences were performed to verify the size of amplification products. Specificity of REP primer/template interactions was demonstrated by amplification between a known REP sequence and a Tn5 insertion in the glpD gene of *E. coli*. The ERIC primers generated PCR products of the expected sizes after amplification of Kohara lambda phages containing the *E. coli* hsdR locus and an adjacent ERIC sequence. Results are shown in FIG. 5. The Kohara lambda phages used are listed by clone numbers and miniset serial numbers are shown in parentheses. One μl of each Kohara phage lysate was used as template DNA. PCR conditions were as described above. Lanes 2–5 represent PCR amplifications with primers within the hsdR gene, hsdR+2758 (SEQ. ID. NO. 58) and hsdR3235R (SEQ. ID. NO. 59). Lanes 7–10 represent PCR products generated by primers hsdR+2758 and ERIC2. Lane 6 is a blank lane where nothing was added to the gel. The molecular weight marker is a 1-kb ladder. The gels were 1% agarose- 1×

Tris-acetate-EDTA and contained 0.5 µg of ethidium bromide per ml. The specificity of ERIC-PCR was confirmed by PCR amplification of a defined DNA segment between a published ERIC sequence, (a/k/a as IRU sequence) and a sequence within the *E. coli* hsdR gene using the ordered Kohara phage library. Single PCR products of the expected size were amplified both within the hsdR gene and between the hsdR and ERIC sequences carried by Kohara phages containing the *E. coli* hsdR locus. Amplification with only a single hsdR primer failed to yield any product.

EXAMPLE 9

Distinguishing Between Strains of Bacteria With REP

Figure 6:
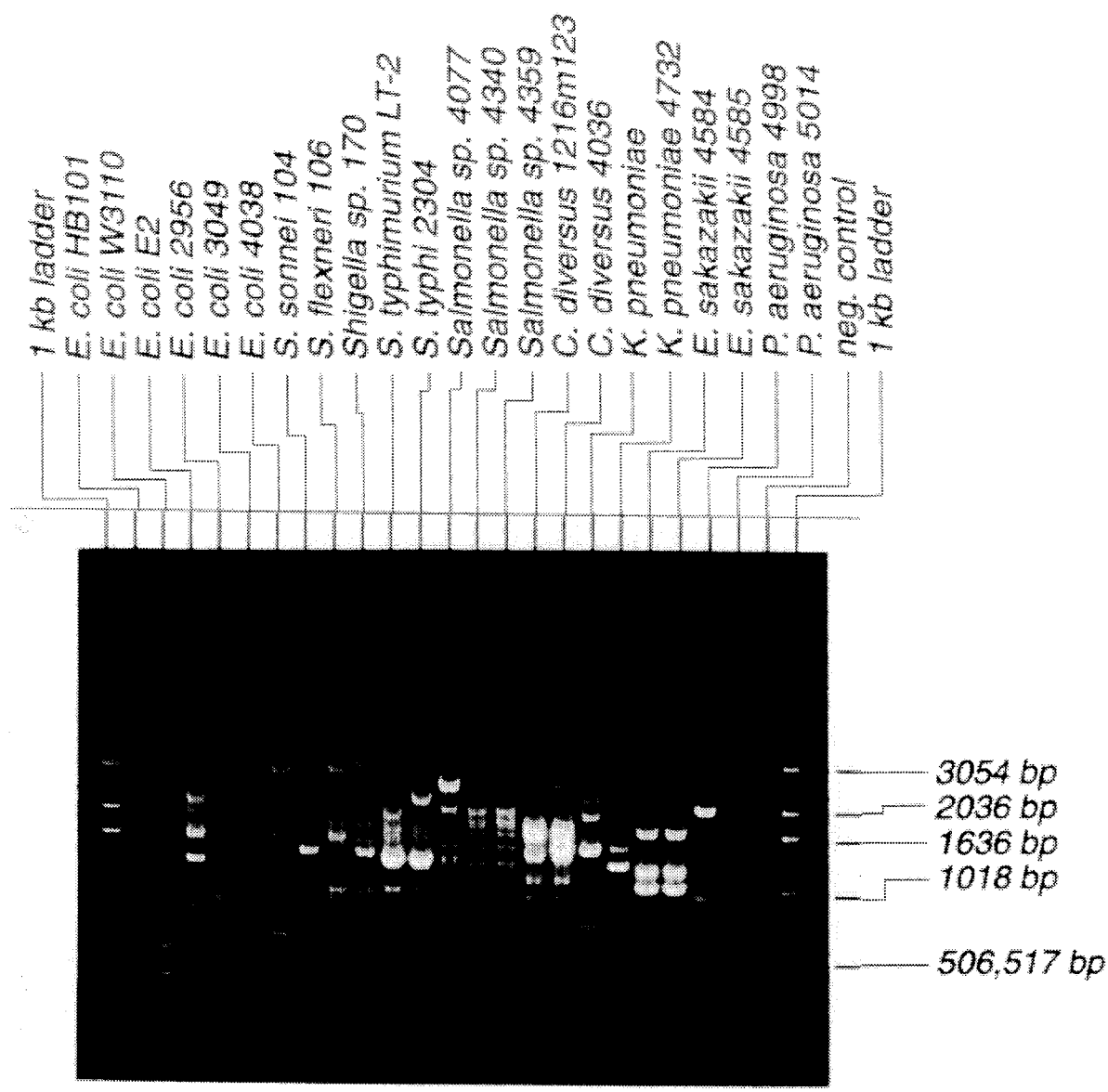
FIG. 6 shows the results of REP-PCR of strains within the Gram-negative enterobacterial species.

REP primers were used to distinguish different strains within Gram-negative enterobacterial species. FIG. 6 shows extension products generated by PCR amplification of enterobacterial genomic DNA with the REP primers, REP1R-I (SEQ. ID. NO. 4) and REP2-I (SEQ. ID. NO.7). PCR reactions were performed as described above. No template DNA was added to the negative control lane. The DNA molecular weight marker is a 1-kb ladder. The gels were 1% agarose-1× Tris-acetate-EDTA and contained 0.5 µg of ethidium bromide per ml.

The REP-PCR genomic fingerprint of different strains from several bacterial species revealed distinct patterns as shown in FIG. 6. PCR amplification of DNA from multiple strains of different enterobacterial species using primers REP1R-I and REP2-I demonstrated subspecies or strain-specific band patterns. Strains within a species could be unambiguously identified. In lanes 2 and 3 (FIG. 6), *E. coli* K-12 strains HB101 and W3110 were distinguished clearly by an extra band of approximately 400 bp in W3110. Laboratory strains of *E. coli* K-12 were related to each other and distinct from the pathogenic strains of *E. coli*. Interestingly the *Salmonella typhimurium* laboratory stain LT-2 revealed a close similarity to *Salmonella typhi* strain 2304. Both of these strains showed REP-PCR patterns clearly distinct from other pathogenic Salmonella strains of undetermined species. The two *Klebsiella pneumoniae* strains shown were obtained from different sources and showed different banding patterns. In lanes 14–15 and lanes 20–21 identical strains of pathogenic Salmonella and *Enterobacter sakazakii* respectively were represented by identical REP-PCR patterns.

EXAMPLE 10

Distinguishing Between Strains of Bacteria With ERIC

Figure 2:
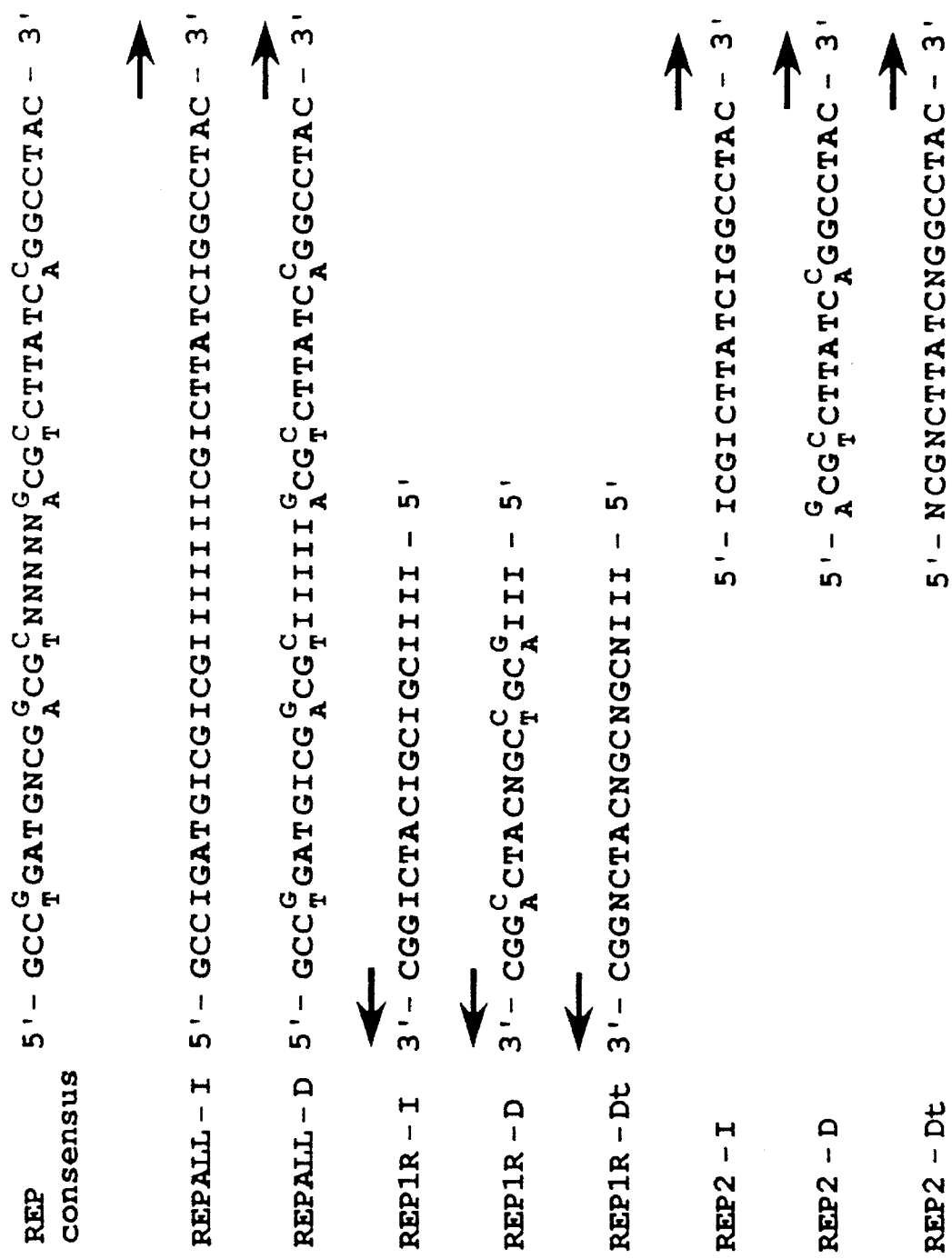
FIG. 2 shows the alignment of various REP oligonucleotide primer sequences with respect to a REP consensus sequence.
Figure 7:
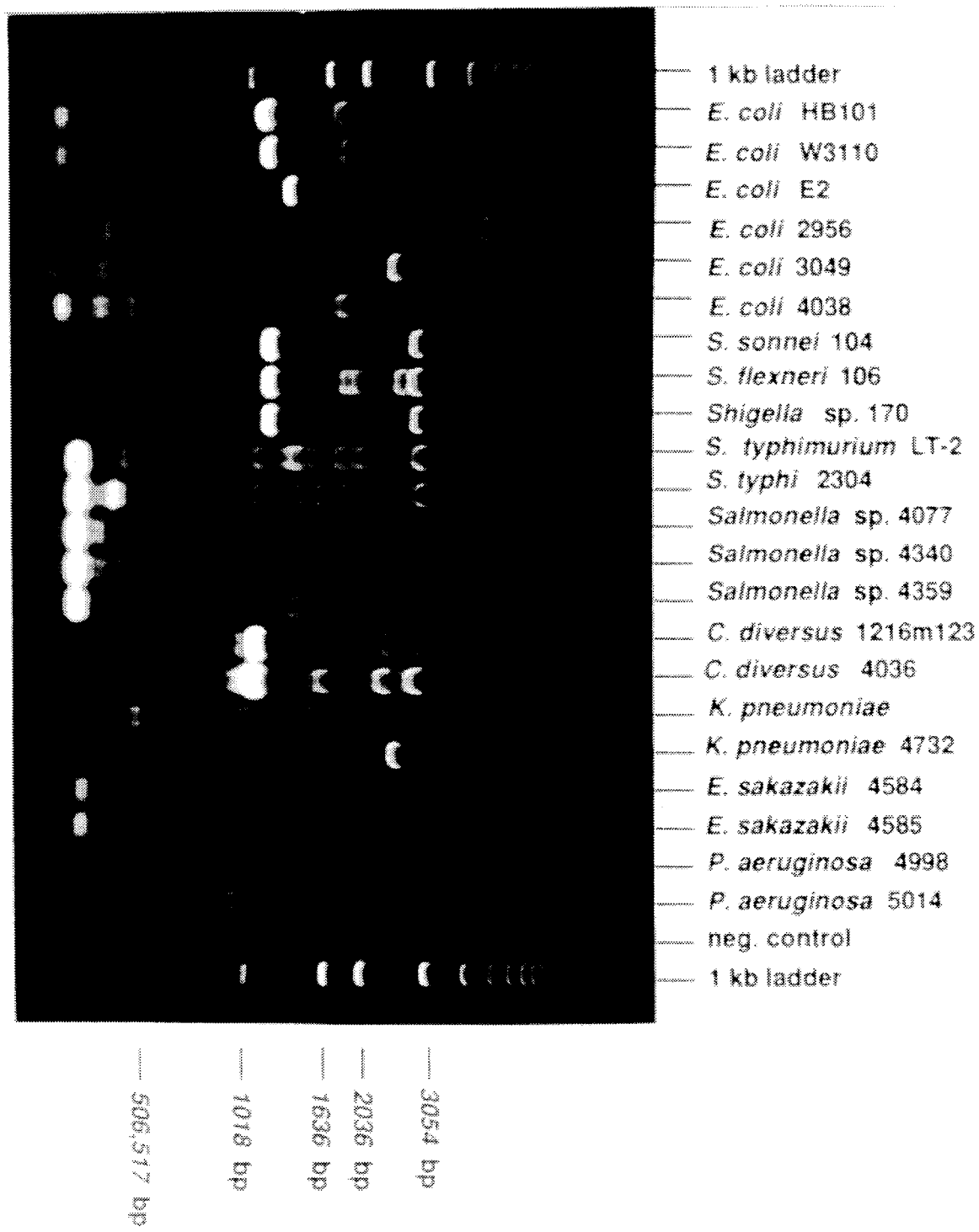
FIG. 7 shows the results of ERIC-PCR of strains within the Gram-negative enterobacterial species.

ERIC primers were used to distinguish different strains within Gram-negative enterobacterial species. FIG. 7 shows extension products generated by PCR amplification of enterobacterial genomic DNA with the ERIC oligonucleotide primers, ERIC1R (SEQ. ID. NO. 38) and ERIC2 (SEQ. ID. NO. 42) (FIG. 2). PCR reactions were performed as described above. No template DNA was added to the negative control lane. The DNA molecular weight marker is a 1-kb ladder. The gels were 1% agarose-1× Tris-acetate-EDTA and contained 0.5 µg of ethidium bromide per ml.

The ERIC-PCR genomic fingerprint of different strains from several bacterial species revealed distinct patterns as shown in FIG. 7. PCR amplification of DNA from multiple strains of different enterobacterial species using primers ERIC1R and ERIC2 demonstrated species specific band patterns. The complexity, however, was less than that obtained with REP-PCR (FIG. 6) and the differences between species were easier to distinguish. This decrease in complexity of the genomic fingerprints, however, made it more difficult to make fine distinctions between strains, for example *E. coli* laboratory strains HB101 and W3110. Greater ERIC-PCR pattern differences existed when comparing laboratory strains of *E. coli* to pathogenic strains of the same species than between laboratory *E. coli* to pathogenic Shigella. The ERIC-PCR patterns of greatest complexity were observed with Salmonella and these results are consistent with previous data base searches revealing an abundance of ERIC in the Salmonella. Because both REP and ERIC PCR yielded common bands between the strains of a given species it provides the ability to group strains within a certain species.

EXAMPLE 11

Evolutionary Conservation of REP Sequences

Figure 9A:
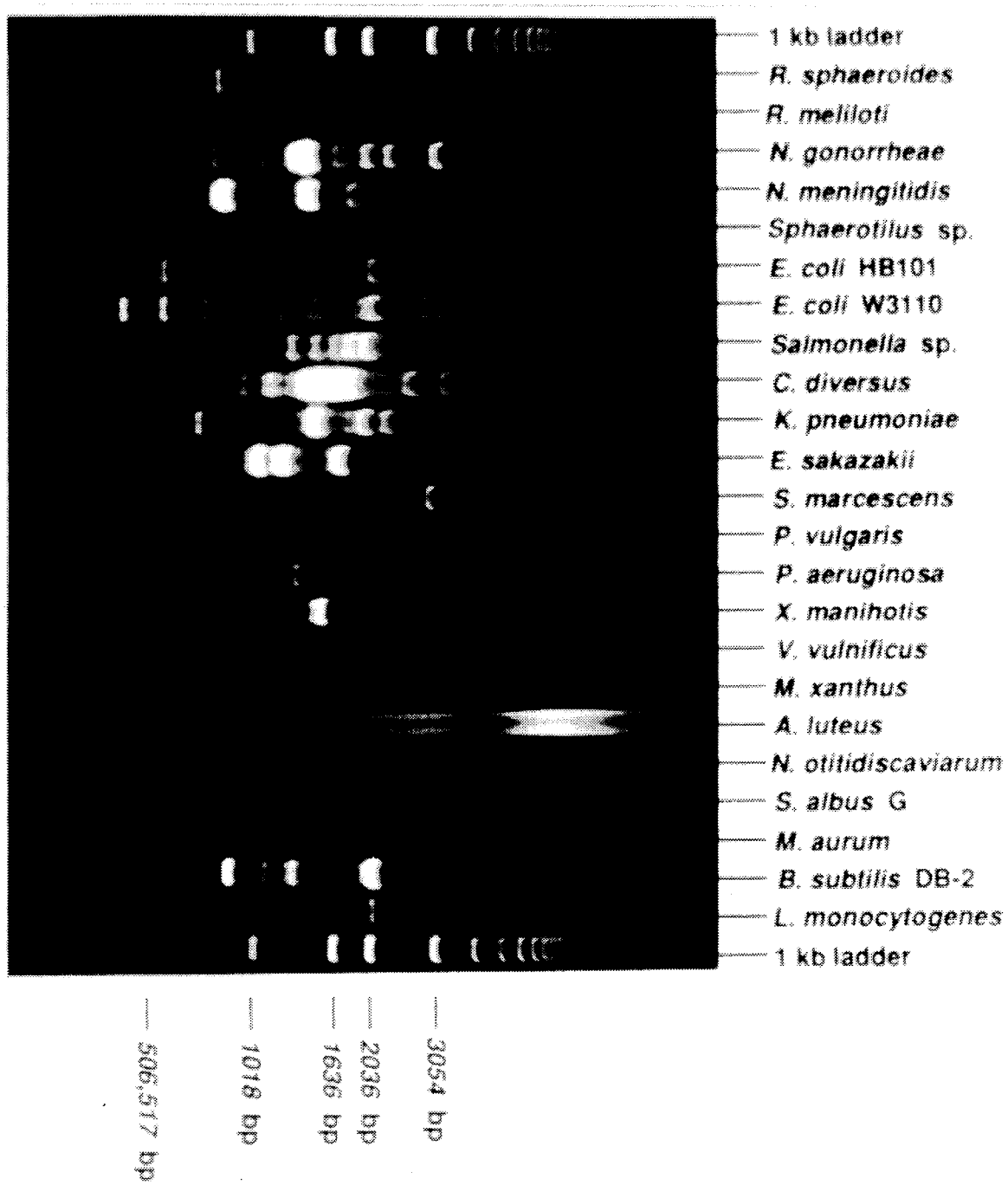
FIGS. 9A and 9B show the evolutionary conservation of REP sequences.
Figure 9B:
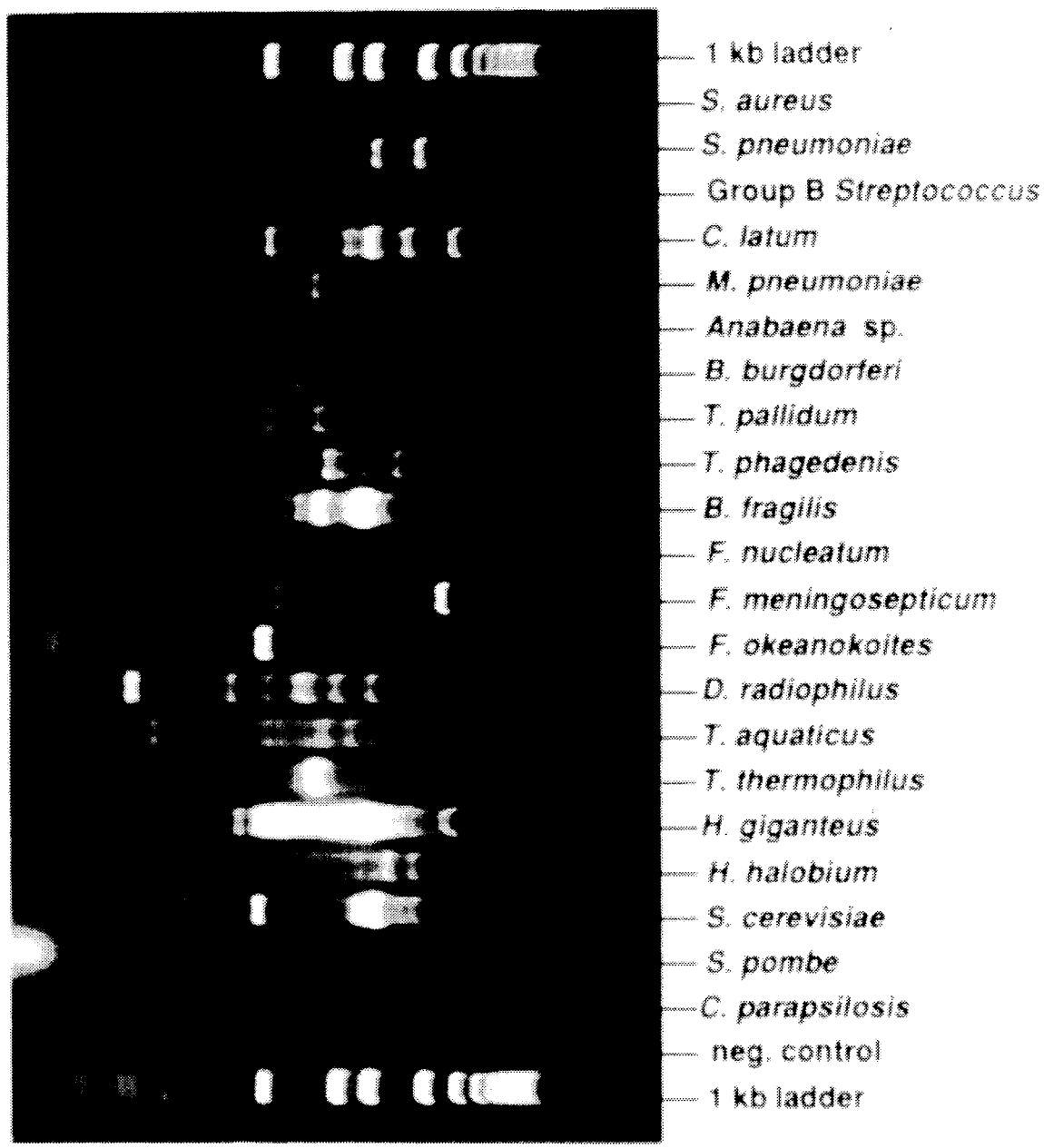

FIGS. 8, 9A and 9B show the use of REP primers to demonstrate the evolutionary conservation of REP sequences. In FIG. 8 is a listing of bacterial and non-bacterial species which match the genomic DNA in each slot of the bug blot hybridization presented in FIG. 8. The bug blot represents a slot blot DNA:DNA hybridization of genomic DNA probed with $^{32}$P-end-labeled REPALL-D (SEQ. ID. NO. 3). Filters were prepared and hybridizations were performed as described above. FIG. 9A and 9B show two gels of PCR amplification products of bacterial genomic DNAs used in the bug blot hybridization with REP primers, REP1R-I and REP2-I. These PCR reactions are presented in exactly the same order as the slots of the bug blot. All PCR reactions were performed as described above. No template DNA was added to the negative control lane. The DNA molecular weight marker is a 1-kb ladder. The gels were 1% agarose-1× Tris-acetate-EDTA and contained 0.5 µg of ethidium bromide per ml.

Slot blot hybridization of the bug blot with SEQ. ID. NO. 3 (FIG. 8) indicates that Gram-negative enterics and related species from the same phyla comprise the majority of REP-positive species. Hybridizations with REPALL-I and REP2-I yielded results similar to the hybridization with REPALL-D. The 38 mer REPALL probes were used for hybridization because the increased length provides a longer homologous stretch and hence greater stability for hybridization. As expected several species of Gram-positive bacteria and spirochetes in addition to the phylogenetically distant eukaryotic fungi failed to yield hybridization signals. Surprisingly, however, hybridization signals were observed with distantly related radioresistant bacteria *Deinococcus radiophilus*, the green non-sulfur bacterium, *Herpetosiphon giganteus*, and the archaebacterium, *Halobacterium halobium*.

PCR amplification of these same bacterial species with primers REP1R-I and REP2-I yielded results consistent with the bug blot hybridization described above. The species that showed the most intense hybridization signals in FIG. 8 generally demonstrated the most complex amplification patterns by REP-PCR (FIGS. 9A and 9B). PCR amplification of genomic DNA from different species clearly revealed species-specific REP-PCR patterns (FIGS. 9A and 9B).

EXAMPLE 12

Evolutionary Conservation of ERIC Sequences

Figure 11A:
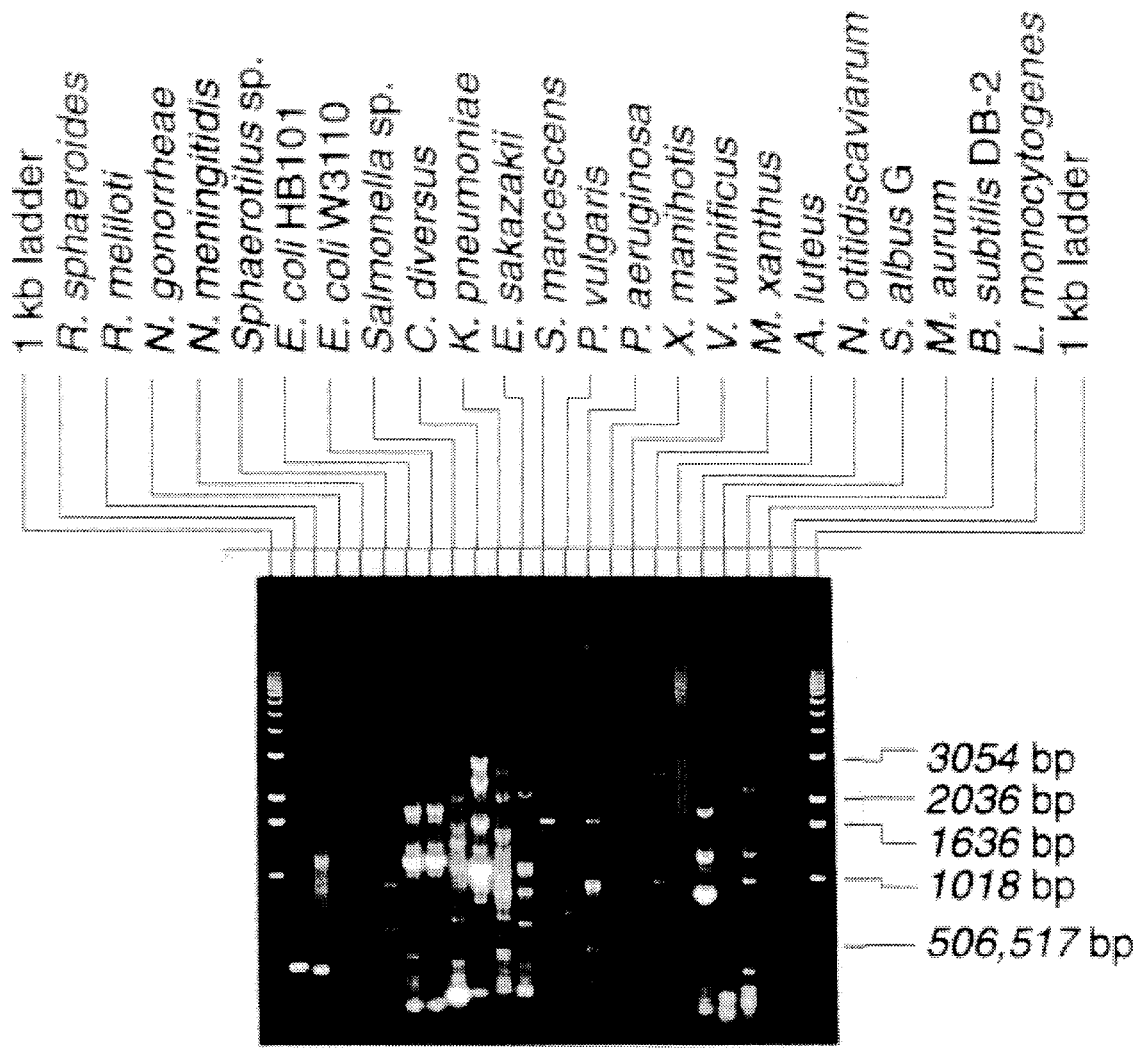
FIGS. 11A and 11B show the evolutionary conservation of ERIC sequences.
Figure 11B:
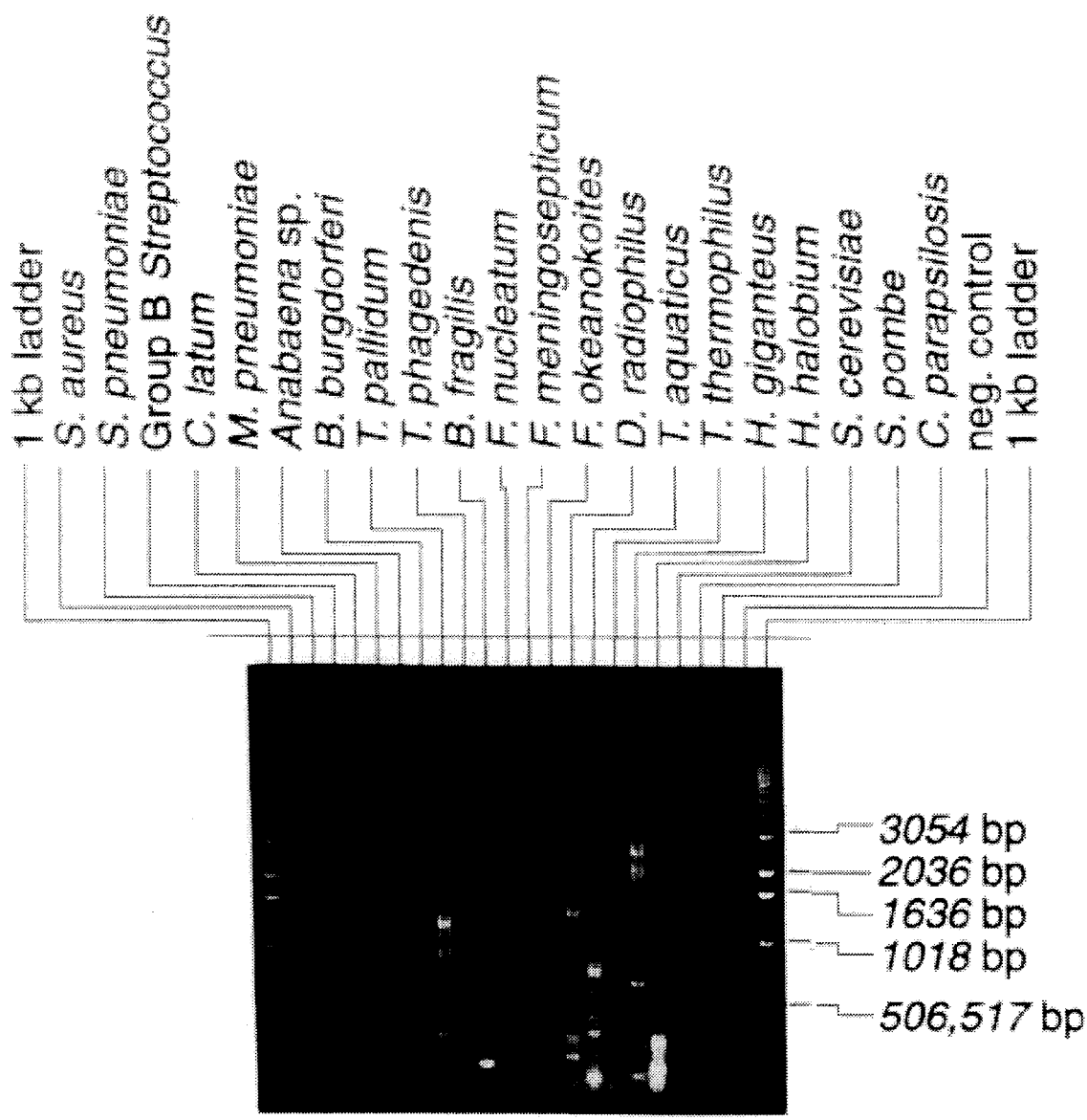

FIGS. 10, 11A and 11B show the use of ERIC primers to demonstrate the evolutionary conservation of ERIC sequences. In FIG. 10 is a listing of bacterial and non-bacterial species which match the genomic DNA in each slot of the bug blot hybridization presented in FIG. 10. The bug blot represents a slot blot DNA:DNA hybridization of genomic DNA probed with $^{32}$P-end-labeled ERIC2. Filters were prepared and hybridizations were performed as described above. FIGS. 11A and 11B show two gels of PCR amplification products from bacterial genomic DNAs used in the bug blot hybridization with the ERIC primers, ERIC1R and ERIC2. These PCR reactions are presented in exactly the same order as the slots of the bug blot. All PCR reactions were performed as described above. No template DNA was added to the negative control lane. The DNA molecular weight marker is a 1-kb ladder. The gels were 1% agarose-1× Tris-acetate-EDTA and contained 0.5 µg/ml of ethidium bromide.

The ERIC primers showed similarity of hybridization and PCR amplification. It should be noted that hybridization with ERICALL yielded results consistent with hybridization with ERIC2. Gram negative enterics and related species from the same family comprised a majority of ERIC positive species and as suspected several species of gram positive bacteria and spirochetes in addition to the fungi failed to yield hybridization signals. Similarly to REP (Ex. 11) the radioresistant, green non-sulfur bacterium and the archaebacterium yielded hybridization signals.

ERIC-PCR also provided results (FIGS. 11A and 11B) consistent with ERIC hybridization of the bug blot (FIG. 10). Gram-negative enteric species yielded the amplification patterns of greatest complexity (FIGS. 11A and 11B). Most Gram-positive species (e.g. *Bacillus subtilis*) showed minimal ERIC-PCR amplification (FIGS. 11A and 11B). This result is consistent with computer searches of ERIC in DNA sequence databases and known phylogenetic distances between Gram-positive bacteria and Gram-negative enteric bacteria.

EXAMPLE 13

Bacterial DNA Fingerprint Library

The method described above was used to screen a plurality of different bacterial strains. The pattern for each strain was categorized and stored. This comprehensive library of fingerprints was used to compare with unknown samples to determine the strain identity.

EXAMPLE 14

Whole Cell PCR

Gram-negative bacterial colonies are picked with disposable loops, and the cells on the edge of the loops are placed directly into PCR tubes containing PCR reaction buffer. The repetitive sequence oligonucleotide primers are then added with dNTP's and DNA polymerase, and the PCR reactions are carried out. Presumably during the initial denaturation step at 94° C. the cells lyse and the chromosomal DNA released into solution serves as the template for PCR amplification. Thus DNA isolation and purification prior to PCR amplification is not always necessary.

EXAMPLE 15

Genome Mapping

REP-PCR was performed on purified cosmid DNA from the ordered Tabata cosmid library. Tabata, et al., J Bacteriol., 171:1214–1218 (1989). This library covers approximately 70% of the *E. coli* strain W3110 genome. This library represents a set of overlapping or isolated cosmids which contain genomic DNA from different locations on the *E. coli* chromosome. Each individual cosmid DNA is purified and used as template DNA in the PCR reaction. 100 ng DNA of each cosmid DNA (represented by serial numbers in FIGS. 14–15) is used as template in REP-PCR with primers REP1R-I and REP2-I (50 pmol of each primer). The PCR products are then electrophoresed in 1% agarose, 1× TAE, and stained with 0.5 micrograms per ml. ethidium bromide.

Figure 14:
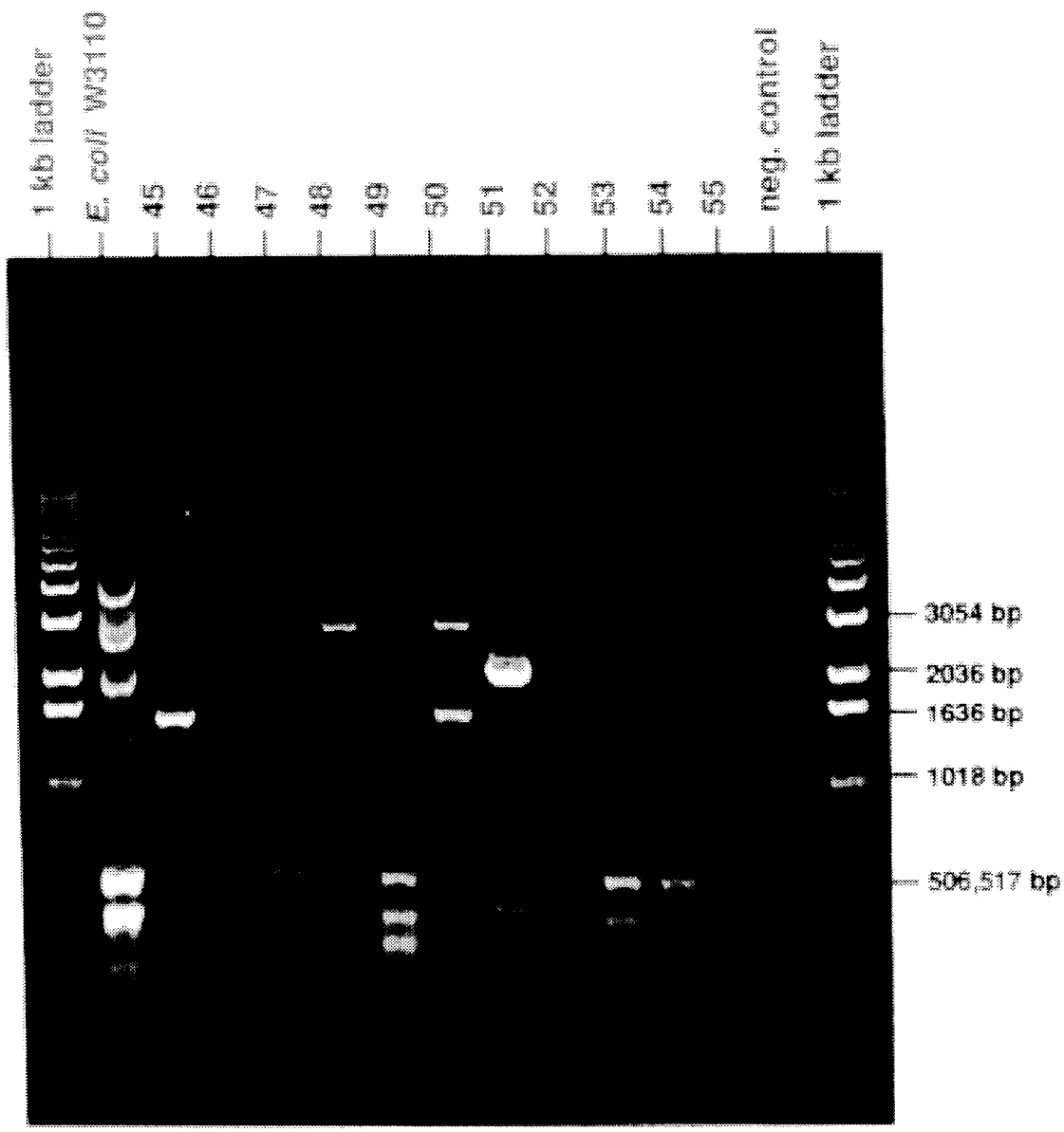
FIG. 14 is REP-PCR of E. coli W3110 genomic cosmid library.
Figure 15:
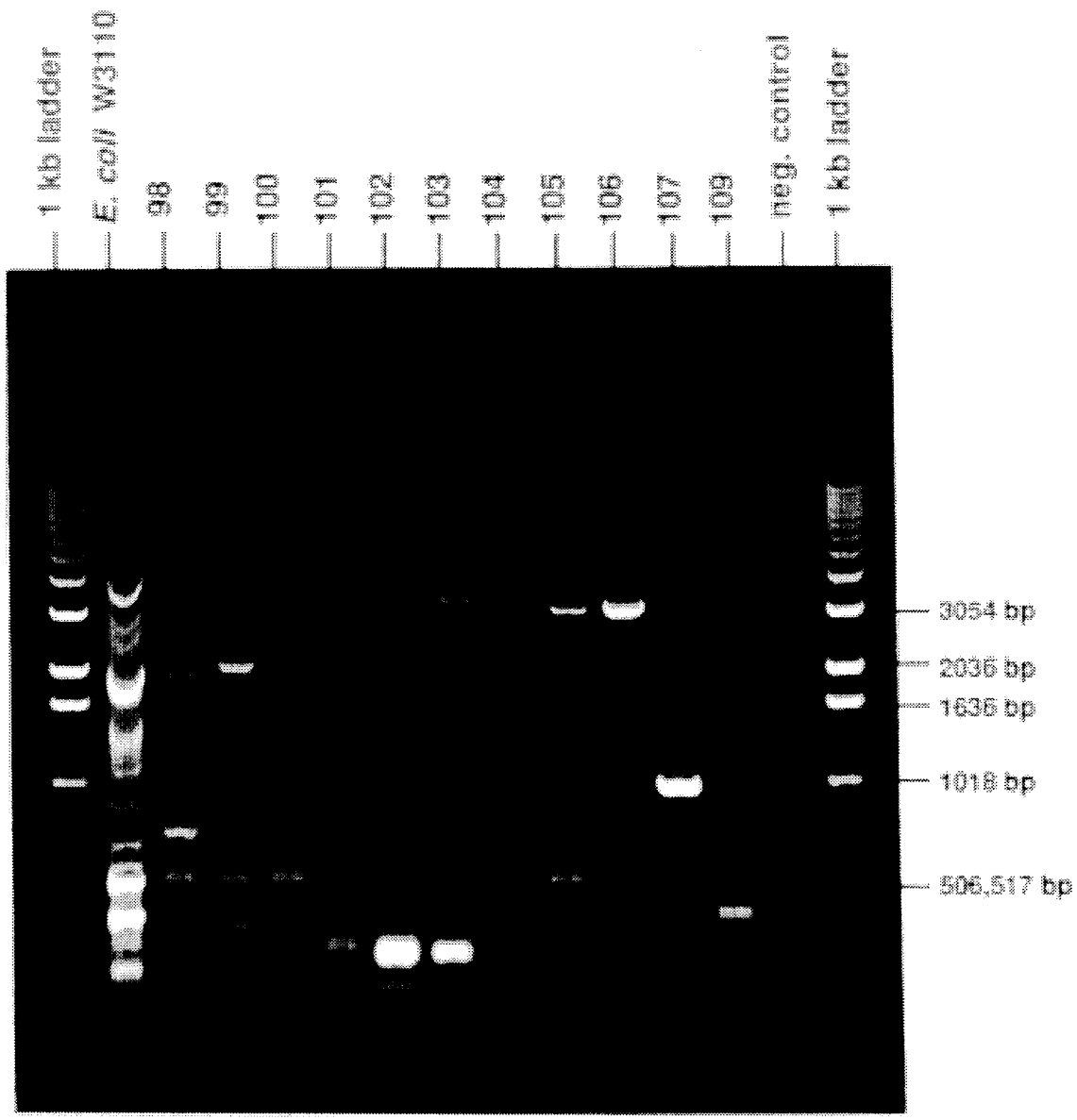
FIG. 15 is REP-PCR of E. coli W3110 genomic cosmid library.

As is evident from FIGS. 14–15, the different cosmids have different REP-PCR fingerprints, depending on which segment of the genome is inserted into a particular clone. By matching fingerprint patterns from individual clones with the computer, contiguous (contigs) and ordered stretches of overlapping clones are built.

Further, this fingerprinting method provides a useful tool for checking the integrity of the library and the purity of each clone. One skilled in the art will readily recognize that these libraries can be made mfrom cosmid, phage, or any possible DNA (even RNA) vector.

EXAMPLE 16

Fingerprinting Bacterial

Strains Used in Newborn Screening

Figure 13:
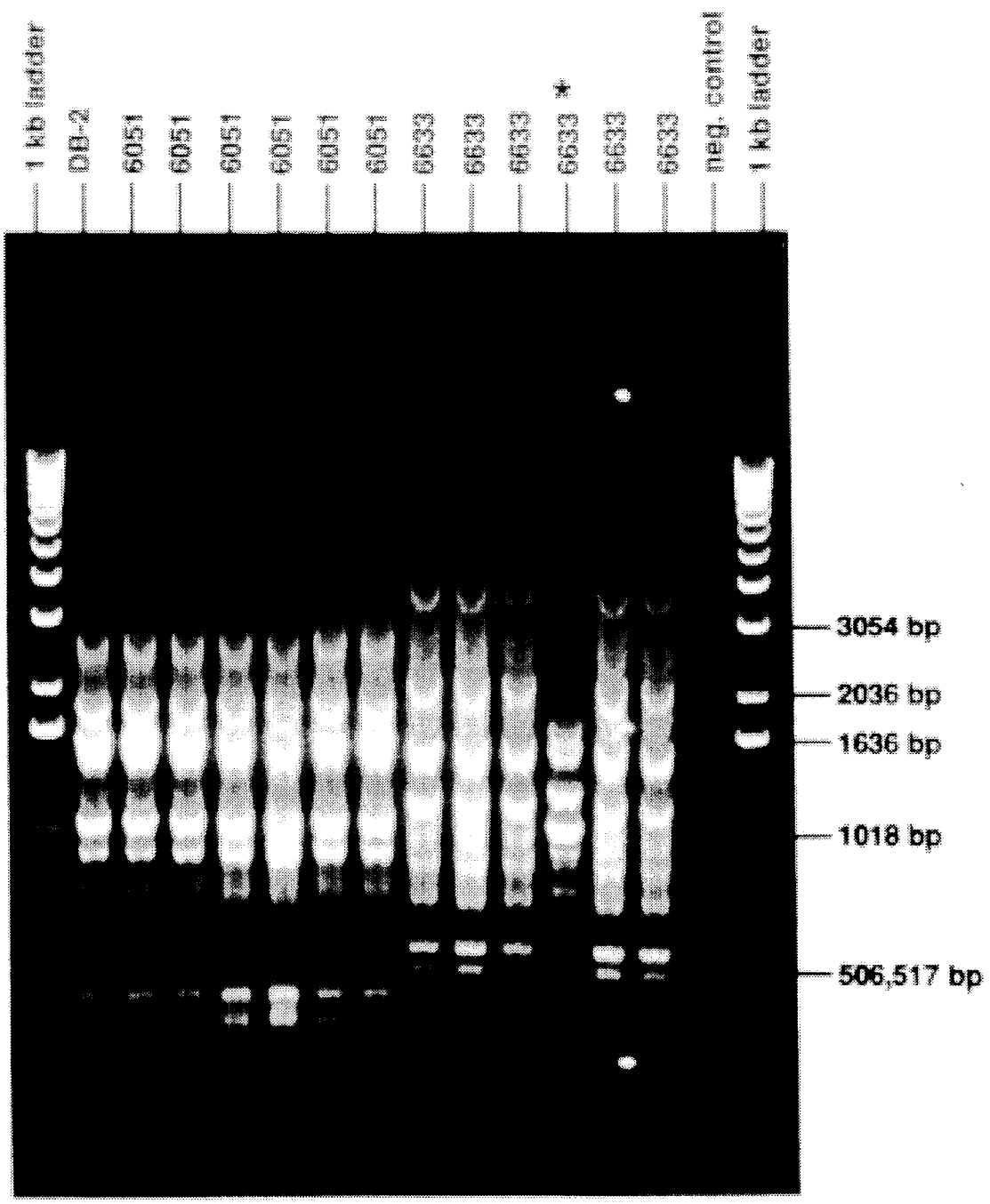
FIG. 13 shows REP/ERIC Fingerprinting of B. subtilis.

The techniques of the present invention were used to monitor the validity of bacterial strains used in newborn screening. REP-PCR, ERIC-PCR, and combined REP/ERIC-PCR were performed on *Bacillus subtilis* strains, ATCC 6633 and 6051, which are used for newborn screening of phenylketonuria (PKU) and maple-syrup urine disease (MSUD) respectively. In the FIG. 13, REP1R-I, REP2-I, ERIC1R, and ERIC2 (50 pmol of each primer) were used in single PCR reactions (REP-ERIC-PCR) on individual samples of *Bacillus subtilis* genomic DNA. One strain that was supposedly ATCC 6633 turned out to be an anomalous strain (lane 12) that was clearly distinct from the others. The strain used for MSUD diagnosis, ATCC 6051, was distinguished from the strain used for PKU diagnosis, ATCC 6633. No template DNA was added to the negative control lane. PCR products were electrophoresed on 1% agarose gels in 1× TAE and stained with 0.5 micrograms per ml. ethidium bromide. It should also be noted that this example shows the combination of two sets of different primers and their simultaneous use in identifying and fingerprinting strains of bacteria.

EXAMPLE 17

Ngrep

Figure 12:
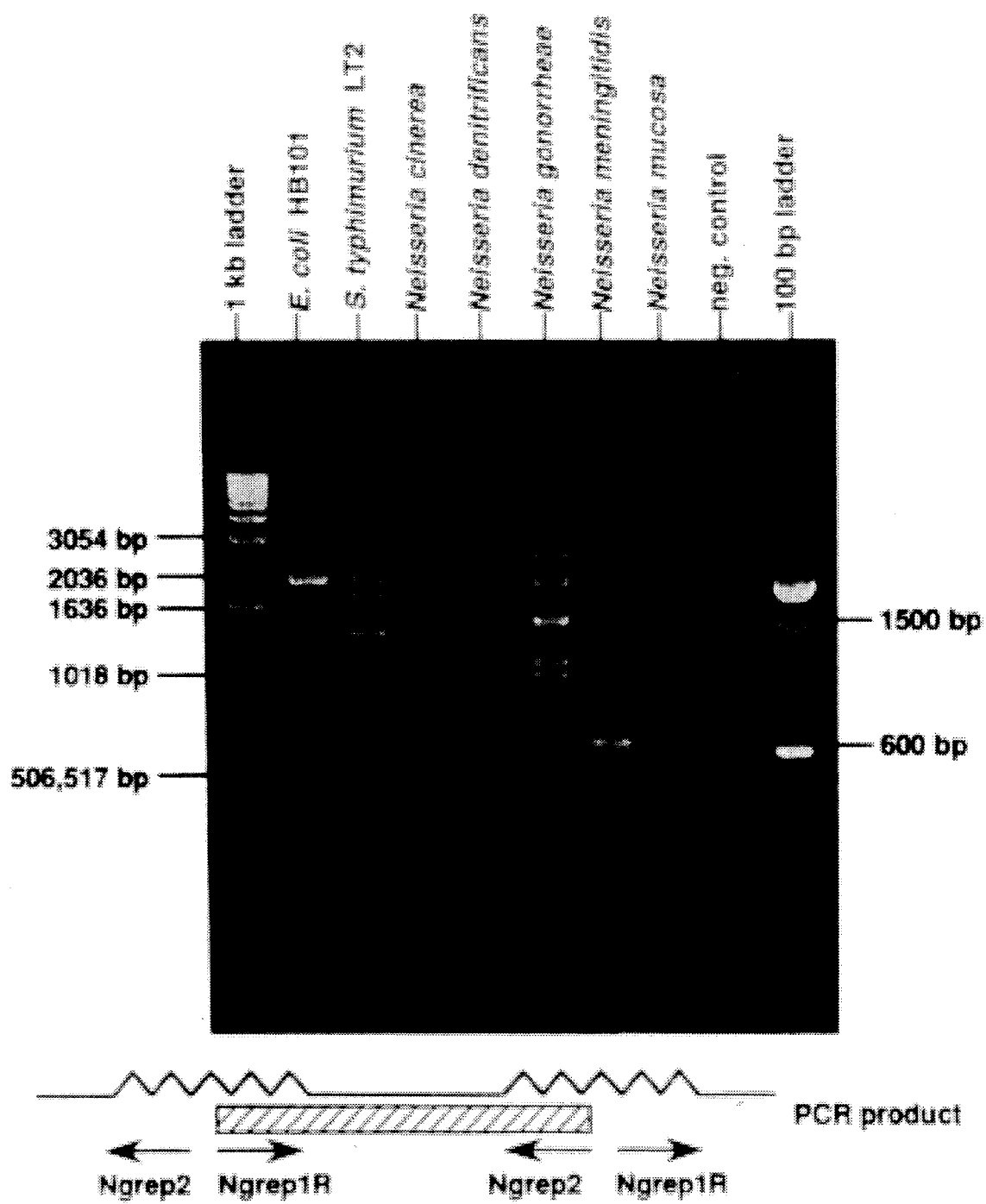
FIG. 12 shows the evolutionary conservation of Ngrep.

In FIG. 12 are the results of PCR using Ngrep primers (SEQ. ID. NOS. 48 and 52). As can be readily seen, the different strains of Neisseria can be distinguished. The conditions are as described in previous examples except the denaturing and annealing steps occur at 94° C. for 1 min. and 38° C. for 1 min., respectively. The negative control has no DNA template but includes primers.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well those inherent therein. The outwardly-directed primers, along with the methods and procedures described herein are presently representative of preferred embodiments, are exemplary, and not intended as limitations on the scope of the invention. Changes therein and other uses will occur to those skilled in the art which are encompassed within the spirit of the invention or defined by the scope of the claims.

---

What we claim is:

1. A method for identifying a species of bacteria, comprising the steps of:
    amplifying DNA between interspersed, non-coding repetitive sequences in a sample containing said bacteria by adding a pair of outwardly-directed primers to said sample, said primers hybridizing to the interspersed, non-coding repetitive DNA sequences in the bacterial DNA and extending outwardly from one hybridizable repetitive sequence to another hybridizable interspersed, non-coding repetitive sequence;
    separating the extension products generated in the amplification step by size; and
    determining the specific species of bacteria by measuring the pattern of sized extension products.

2. The method of claim 1 wherein the hybridizable repetitive sequence is selected from the group consisting of repetitive extragenic palindromic elements (REP), enterobacterial repetitive intergenic consensus sequence (ERIC), Neisseria repetitive extragenic elements (Ngrep), Deinococcus repetitive extragenic elements (Drrep) and any combination thereof.

3. The method of claim 1, wherein the primers are between about 10 and 29 nucleotides.

4. The method of claim 1 wherein the primers are 15 to 25 nucleotides.

5. The method of claim 1 wherein the repetitive sequence is REP and one member of the pair of primers is selected from the group consisting of SEQ. ID. Nos. 4, 5, 6, 10, 11, 12, 13, 14, 15, 16, 17, 18, 19, 20, 21 and 34; and the other member of the pair is selected from the group consisting of SEQ. ID. NOS. 7, 8, 9, 22, 23, 24, 25, 26, 27, 28, 29, 30, 31, 32, 33 and 35.

6. The method of claim 1, wherein the repetitive sequence is ERIC and one member of the pair of primers is selected from the group consisting of SEQ. ID. NOS. 38, 39, 40 and 41; and the other member of the pair is selected from the group consisting of SEQ. ID. NOS. 42, 43, 44 and 45.

7. The method of claim 1, wherein the repetitive sequence is Ngrep and one member of the pair of primers is selected from the group consisting of SEQ. ID. NOS. 48, 49, 50 and 51; and the other member of the pair is selected from the group consisting of 52, 53, 54 and 55.

8. The method of claim 1, wherein the primers are SEQ. ID. NO. 4 and SEQ. ID. NO. 7.

9. The method of claim 1, wherein the repetitive sequence is ERIC and the primers are SEQ. ID. NO. 38 and SEQ. ID. NO. 42.

10. The method of claim 1, wherein the repetitive sequence is Ngrep and the primers are SEQ. ID. NO. 48 and SEQ. ID. NO. 52.

11. The method of claim 1, wherein the repetitive sequence is Drrep and the primer is SEQ. ID. NO. 56 or SEQ. ID. NO. 57.

12. The method of claim 1, wherein a plurality of pairs are added and wherein each pair is to a different repetitive sequence.

13. The method of claim 12, wherein primers are selected from the group consisting of REP, ERIC, Ngrep, Drrep and any combination thereof.

14. The method of claim 12, wherein the primers are SEQ. ID. NOS. 4, 7, 38 and 42.

15. The method of claim 1, wherein the DNA is extracted from the bacteria prior to adding the primers.

16. The method of claim 1, wherein the separating step includes gel electrophoresis of the extension products.

17. The method of claim 16, wherein the extension products are stained with ethidium bromide.

18. The method of claim 1 wherein the primers are labelled and the determining step includes measuring the pattern of labelling.

19. The method of claim 1 wherein the separation step includes chromatography of the extension products.

20. The method of claim 19, wherein the primers are labelled.

21. The method of claim 19, wherein the label is a fluorescer.

22. The method of claim 1, wherein the sample contains a plurality of species of bacteria and wherein each specific species of bacteria is distinguished by comparing the size pattern of extension products to a library of known fingerprints to determine the identity of each specific species of bacteria in the sample.

23. The method of claim 1, wherein the sample contains a plurality of species of bacteria and wherein each specific species of bacteria is isolated prior to the amplification step.

24. The method of claim 22 or 23 wherein the sample is selected from the group consisting of blood, urine, spinal fluid, tissue, vaginal swab, stool, amniotic fluid, and buccal mouthwash.

25. The method of claim 24, wherein the sample is from a human subject.

26. The method of claim 24, wherein the test sample is from an animal subject.

27. The method of claim 22 or 23, wherein the test sample is an agriculture sample.

28. The method of claim 22 or 23, wherein the test sample is food.

29. The method of claim 22 or 23, where in the test sample is an environmental sample.

30. The method of claim 22 or 23, wherein the test sample is a horticulture sample.

31. The method of claim 1 for diagnosing bacterial disease wherein the sample is collected from a subject suspected of having a bacterial disease.

32. The method of claim 31, wherein the subject is a human.

33. The method of claim 31, wherein the subject is an animal.

34. The method of claim 31, wherein the subject is a plant.

35. The method of claim 1 for monitoring bacterial contamination in an environment wherein the sample is collected from an environmental source suspected of being contaminated.

36. The method of claim 35, wherein the environmental source is a liquid.

37. The method of claim 35, wherein the environmental source is sludge.

38. The method of claim 35, wherein the environmental source is sewage.

39. The method of claim 35, wherein the environmental source is a treatment plant.

40. The method of claim 35, wherein the environmental source is soil.

41. The method of claim 1 for monitoring bacterial contamination of food wherein the sample is collected from food suspected of being contaminated.

42. The method of claim 41, wherein the food is infant formula.

43. The method of claim 41, wherein the food is sea food.

44. The method of claim 41, wherein the food is fresh produce.

45. The method of claim 41, wherein the food is processed food.

46. The method of claim 1 for monitoring a bacterial population at a bioremediation site wherein the sample is collected from said site.

47. The method of claim 46, wherein the sample is soil.

48. The method of claim 46, wherein the sample is liquid.

49. The method of claim 46, wherein the sample is sludge.

50. The method of claim 46, wherein the sample is from the bacteria which is to be added to the site.

51. The method of claim 1 for monitoring a horticulture sample wherein the sample is collected from a horticulture source to be tested.

52. The method of claim 1 for monitoring an agriculture sample wherein the sample is collected from an agriculture source to be tested.

53. The method of claim 1 for monitoring bacterial additions to an agricultural environment wherein the sample is collected from an agriculture source to be tested.

54. The method of claim 53, wherein the sample is a liquid.

55. The method of claim 53, wherein the sample is soil.

56. The method of claim 53, wherein the sample is from a plant.

57. The method of claim 53, wherein the sample is from an animal.

58. The method of claim 1 for monitoring manufacturing processes for bacteria wherein the sample is collected from the process to be tested.

59. The method of claim 58, wherein the sample is selected from the group consisting of drug manufacturing processes, fermentation processes, microorganism-aided synthesis processes, chemical manufacturing process and food manufacturing processes.

60. The method of claim 1 for quality assurance/quality control of laboratory tests involving microbiological assays wherein the sample is collected from the bacterial stock to be tested.

61. The method of claim 1 for tracing outbreaks of bacterial infections, wherein the sample is collected from an organism to be tested.

62. A method for genome mapping, comprising the steps of:

fractionating the genome;

cloning the fractionated genome into a vector;

testing the cloned vectors by amplifying bacterial DNA in the clones by adding a pair of outwardly-directed primers to the test sample, said primers capable of hybridizing to repetitive DNA sequences in the bacterial DNA and extending outwardly from the hybridizable repetitive sequence to another hybridizable repetitive sequence;

separating the extension products of the amplification step by size; and measuring the pattern of extension products; and reconstructing the genome from the overlapping patterns.

63. A method for automated identification of a strain of bacteria comprising the steps of:

adding bacteria and outwardly-directed PCR primers to a test sample in an auto-PCR instrument, wherein said primers are capable of hybridizing to repetitive DNA sequence in the bacterial DNA and extending outwardly from the hybridizable repetitive sequence to another hybridizable repetitive sequence;

transferring the extension products from the PCR assay and separating the extension products;

measuring the sizing pattern of said separated extension products with a measuring means; and recognizing and identifying the sizing pattern by a computer means.

64. A method for the automated identification of a species of bacteria comprising the steps of:

adding bacteria and outwardly-directed PCR primers to a test sample in an auto-PCR-instrument, wherein said primers are capable of hybridizing to repetitive DNA sequence in a bacteria DNA and extending outwardly from the hybridizable repetitive sequence to another hybridizable repetitive sequence, transferring the extension products from the PCR assay and separating the extension products;

measuring the sizing pattern of said separated extension products with a measuring means; and recognizing and identifying the sizing pattern by a computer means.

65. The method of claim 63 or 64, wherein the measuring means is selected from the group consisting of a bar code reader, a laser reader, a digitizer, a photometer and a fluorescence reader.

66. The method of claim 63 or 64 wherein the extension products are separated by chromatography or gel electrophoresis.

67. The method of 63 or 64, wherein a sample from the PCR amplification is applied to a gel and electrophoresed; the size pattern is read by a measuring means; and the pattern is compared by the computer means with stored known bacterial patterns.

68. The method of 63 or 64, wherein the separated extension products are stained with ethidium bromide before reading.

69. The method of 63 or 64, wherein the primers are labelled.

70. The method of 63 or 64, wherein the primers are labelled with fluorescer.

71. A method of identifying a species of bacteria in a test sample, comprising the steps of:

amplifying DNA in said bacteria by adding a plurality of pairs of outwardly-directed primers to said test sample, each pair of said primers hybridizing to different interspersed, non-coding repetitive DNA sequences in the bacterial DNA and each pair extending outwardly from one hybridizable interspersed, non-coding repetitive sequence to another hybridizable interspersed, non-coding repetitive sequence and wherein each pair is differentially labelled;

separating the extension products generated in the amplification step by size;

determining the specific species of bacteria by measuring the pattern of sized extension products for each pair.

72. The method of 71, wherein the labels are fluorescers.

73. The method of 71, wherein the separation is by gel electrophoresis, capillary electrophoresis, mass spectrometry or chromatography.

74. The method of claim 71, wherein the primer pairs are selected from the group consisting of REP, ERIC, Ngrep, Drrep and any combination thereof.

75. A kit for determining the identity of species of bacteria, comprising a container having outwardly-directed PCR primer pairs to repetitive sequences in bacteria.

76. The kit of claim 75, wherein the PCR primer pairs are selected from the group consisting of SEQ. ID. NOS. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 38, 39, 40, 41, 42, 43, 44, 45, 48, 49, 50, 51, 52, 53, 54, 55, 56, 57 and any combination thereof.

77. As a composition of matter the DNA oligonucleotides selected from the group consisting of SEQ. ID. NOS. 4, 5, 6, 7, 8, 9, 10, 11, 12, 13, 14, 15, 16, 17, 18, 19, 20, 21, 22, 23, 24, 25, 26, 27, 28, 29, 30, 31, 32 and 33.

78. As a composition of matter the DNA oligonucleotides selected from the group consisting of SEQ. ID. NOS. 38, 39, 40, 41, 42, 43, 44 and 45.

79. As a composition of matter the DNA oligonucleotides selected from the group consisting of SEQ. ID. NOS. 48, 49, 50, 51, 52, 53, 54 and 55.

80. As a composition of matter the DNA oligonucleotides selected from the group consisting of SEQ. ID. NOS. 56 and 57.

81. As a composition of matter DNA oligonucleotides selected from the group consisting of SEQ. ID. NOS. 4 and 7.

82. As a composition of matter DNA oligonucleotides selected from the group consisting of SEQ. ID. NOS. 38 and 42.

83. As a composition of matter DNA oligonucleotides selected from the group consisting of SEQ. ID. NOS. 48 and 52.

84. The method of claim 1 or 69, wherein the sample is tested for bacterial contamination and the sample is stored blood or blood used for transfusions.

85. The method of claim 82, wherein the sample is tested for the specific bacterial species Yersinia enterocolitica.

86. A method for identifying a species of bacteria, comprising the steps of:

amplifying DNA between interspersed, non-coding repetitive sequences in a sample containing said bacteria by adding a primer to said sample, wherein said primer hybridizes to the interspersed, non-coding repetitive sequence in either of the complementary strands of the DNA and wherein the hybridized primer extends from one interspersed, non-coding repetitive sequence across non-repetitive DNA to another interspersed, non-coding repetitive sequence and wherein said extension product hybridizes to the primer for generations of further extension products;

separating the extension products by size; and determining the specific species of bacteria by measuring the pattern of sized extension products.

87. A method for differentiating a strain in the same species of bacteria, comprising the steps of:

amplifying DNA between repetitive sequences in a sample containing said bacteria by adding a pair of outwardly-directed primers to said sample, said primers capable of hybridizing to repetitive DNA sequences in the bacterial DNA and extending outwardly from one hybridizable repetitive sequence to another hybridizable repetitive sequence;

separating the extension products generated in the amplification step by size; and determining the specific strain of bacteria by measuring the pattern of sized extension products.

88. The method of claim 87 wherein the hybridizable repetitive sequence is selected from the group consisting of repetitive extragenic palindromic elements (REP), enterobacterial repetitive intergenic consensus sequence (ERIC), Neisseria repetitive extragenic elements (Ngrep), Deinococcus repetitive extragenic elements (Drrep) and any combination thereof.

89. The method of claim 87, wherein the primers are between about 10 and 29 nucleotides.

90. The method of claim 87 wherein the primers are 15 to 25 nucleotides.

91. The method of claim 87 wherein the repetitive sequence is REP and one member of the pair of primers is selected from the group consisting of SEQ. ID. Nos. 4, 5, 6, 10, 11, 12, 13, 14, 15, 16, 17, 18, 19, 20, 21 and 34; and the other member of the pair is selected from the group consisting of SEQ. ID. NOS. 7, 8, 9, 22, 23, 24, 25, 26, 27, 28, 29, 30, 31, 32, 33 and 35.

92. The method of claim 87, wherein the repetitive sequence is ERIC and one member of the pair of primers is selected from the group consisting of SEQ. ID. NOS. 38, 39, 40 and 41; and the other member of the pair is selected from the group consisting of SEQ. ID. NOS. 42, 43, 44 and 45.

93. The method of claim 87, wherein the repetitive sequence is Ngrep and one member of the pair of primers is selected from the group consisting of SEQ. ID. NOS. 48, 49, 50 and 51; and the other member of the pair is selected from the group consisting of 52, 53, 54 and 55.

94. The method of claim 87, wherein the primers are SEQ. ID. NO. 4 and SEQ. ID. NO. 7.

95. The method of claim 87, wherein the repetitive sequence is ERIC and the primers are SEQ. ID. NO. 38 and SEQ. ID. NO. 42.

96. The method of claim 87, wherein the repetitive sequence is Ngrep and the primers are SEQ. ID. NO. 48 and SEQ. ID. NO. 52.

97. The method of claim 87, wherein the repetitive sequence is Drrep and the primer is SEQ. ID. NO. 56 or SEQ. ID. NO. 57.

98. The method of claim 87, wherein a plurality of pairs are added and wherein each pair is to a different repetitive sequence.

99. The method of claim 98, wherein primers are selected from the group consisting of REP, ERIC, Ngrep, Drrep and any combination thereof.

100. The method of claim 98, wherein the primers are SEQ. ID. NOS. 4, 7, 38 and 42.

101. The method of claim 87, wherein the DNA is extracted from the bacteria prior to adding the primers.

102. The method of claim 87, wherein the separating step includes gel electrophoresis of the extension products.

103. The method of claim 102, wherein the extension products are stained with ethidium bromide.

104. The method of claim 87 wherein the primers are labelled and the determining step includes measuring the pattern of labelling.

105. The method of claim 87 wherein the separation step includes chromatography of the extension products.

106. The method of claim 105, wherein the primers are labelled.

107. The method of claim 105, wherein the label is a fluorescer.

108. The method of claim 87, wherein the sample contains a plurality of strains of bacteria, and wherein each specific strain of bacteria is distinguished by comparing the size pattern of extension products to a library of known fingerprints to determine species identity.

109. The method of claim 87, wherein the sample contains a plurality of strains of bacteria and wherein each specific strain of bacteria is isolated prior to the amplification step.

110. The method of claim 108 or 109, wherein the sample is selected from the group consisting of blood, urine, spinal fluid, tissue, vaginal swab, stool, amniotic fluid, and buccal mouthwash.

111. The method of claim 110, wherein the sample is from a human subject.

112. The method of claim 110, wherein the test sample is from an animal subject.

113. The method of claim 108 or 109, wherein the test sample is an agriculture sample.

114. The method of claim 108 or 109, wherein the test sample is food.

115. The method of claim 108 or 109, wherein the test sample is an environmental sample.

116. The method of claim 108 or 109, wherein the test sample is a horticulture sample.

117. The method of claim 87 for diagnosing bacterial disease wherein the sample is collected from a subject suspected of having a bacterial disease.

118. The method of claim 117, wherein the subject is a human.

119. The method of claim 117, wherein the subject is an animal.

120. The method of claim 117, wherein the subject is a plant.

121. The method of claim 87 for monitoring bacterial contamination in an environment wherein the sample is collected from an environmental source suspected of being contaminated.

122. The method of claim 121, wherein the environmental source is a liquid.

123. The method of claim 121, wherein the environmental source is sludge.

124. The method of claim 121, wherein the environmental source is sewage.

125. The method of claim 121, wherein the environmental source is a treatment plant.

126. The method of claim 121, wherein the environmental source is soil.

127. The method of claim 87 for monitoring bacterial contamination of food wherein the sample is collected from food suspected of being contaminated.

128. The method of claim 127, wherein the food is infant formula.

129. The method of claim 127, wherein the food is sea food.

130. The method of claim 127, wherein the food is fresh produce.

131. The method of claim 127, wherein the food is processed food.

132. The method of claim 87 for monitoring a bacterial population at a bioremediation site wherein the sample is collected from said site.

133. The method of claim 132, wherein the sample is soil.

134. The method of claim 132, wherein the sample is liquid.

135. The method of claim 132, wherein the sample is sludge.

136. The method of claim 132, wherein the sample is from the bacteria which is to be added to the site.

137. The method of claim 87 for monitoring a horticulture sample wherein the sample is collected from a horticulture source to be tested.

138. The method of claim 87 for monitoring an agriculture sample wherein the sample is collected from an agriculture source to be tested.

139. The method of claim 87 for monitoring bacterial additions to an agricultural environment wherein the sample is collected from an agriculture source to be tested.

140. The method of claim 139, wherein the sample is a liquid.

141. The method of claim 139, wherein the sample is soil.

142. The method of claim 139, wherein the sample is from a plant.

143. The method of claim 139, wherein the sample is from an animal.

144. The method of claim 87 for monitoring manufacturing processes for bacteria wherein the sample is collected from the process to be tested.

145. The method of claim 144, wherein the sample is selected from the group consisting of drug manufacturing processes, fermentation processes, microorganism-aided synthesis processes, chemical manufacturing process and food manufacturing processes.

146. The method of claim 87 for quality assurance/quality control of laboratory tests involving microbiological assays wherein the sample is collected from the bacterial stock to be tested.

147. The method of claim 87 for tracing outbreaks of bacterial infections, wherein the sample is collected from an organism to be tested.

148. A method of differentiating a strain in the same species of bacteria in a test sample, comprising the steps of:
  amplifying DNA in said bacteria by adding a plurality of pairs of outwardly-directed primers to said test sample, each pair of said primers hybridizing to different repetitive DNA sequences in the bacterial DNA and each pair extending outwardly from one hybridizable repetitive sequence to another hybridizable repetitive sequence and wherein each pair is differentially labelled;
  separating the extension products generated in the amplification step by size;
  determining the specific strain of bacteria by measuring the pattern of sized extension products for each pair.

149. The method of 148, wherein the labels are fluorescers.

150. The method of 148, wherein the separation is by gel electrophoresis, capillary electrophoresis, mass spectrometry or chromatography.

151. The method of claim 148, wherein the primer pairs are selected from the group consisting of REP, ERIC, Ngrep, Drrep and any combination thereof.

152. A kit for determining the identity of a strain of bacteria, comprising a container having outwardly-directed PCR primer pairs to repetitive sequences in bacteria.

153. The kit of claim 152, wherein the PCR primer pairs are selected from the group consisting of SEQ. ID. NOS. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 38, 39, 40, 41, 42, 43, 44, 45, 48, 49, 50, 51, 52, 53, 54, 55, 56, 57 and any combination thereof.

154. The method of claim 87 or 148, wherein the blood sample is tested for bacterial contamination and the sample is stored blood or blood used for transfusions.

155. The method of claim 154, wherein the sample is tested for the specific bacterial species Yersinia enterocolitica.

156. A method for identifying a strain in the same species of bacteria, comprising the steps of:
  amplifying DNA between repetitive sequences in a sample containing said bacteria by adding a primer to said sample, wherein said primer hybridizes to the repetitive sequence in either of the complementary strands of the DNA and wherein the hybridized primer extends from one repetitive sequence across non-repetitive DNA to another repetitive sequence and wherein said extension product hybridizes to the primer for generations of further extension products;
  separating the extension products by size; and
  determining the specific strain of bacteria by measuring the pattern of sized extension products.

* * * * *